US011052259B2

(12) United States Patent
Stinauer et al.

(10) Patent No.: US 11,052,259 B2
(45) Date of Patent: Jul. 6, 2021

(54) CONNECTOR ASSEMBLY FOR AN ELECTRICAL STIMULATION SYSTEM AND METHODS OF MAKING AND USING

(71) Applicant: Boston Scientific Neuromodulation Corporation, Valencia, CA (US)

(72) Inventors: Robert J. Stinauer, Valencia, CA (US); David M. Dorman, Castaic, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 75 days.

(21) Appl. No.: 16/405,316

(22) Filed: May 7, 2019

(65) Prior Publication Data
US 2019/0344085 A1    Nov. 14, 2019

Related U.S. Application Data

(60) Provisional application No. 62/670,412, filed on May 11, 2018.

(51) Int. Cl.
*A61N 1/375*    (2006.01)
*A61N 1/36*    (2006.01)
(Continued)

(52) U.S. Cl.
CPC ....... *A61N 1/3754* (2013.01); *A61N 1/36128* (2013.01); *H01R 13/22* (2013.01);
(Continued)

(58) Field of Classification Search
CPC .............. A61N 1/3754; A61N 1/36128; A61N 1/36071; A61N 1/3614; A61N 1/36135;
(Continued)

(56) References Cited

U.S. PATENT DOCUMENTS 3,222,471 A    12/1965 Steinkamp
3,601,747 A    8/1971 Prall et al.
(Continued)

FOREIGN PATENT DOCUMENTS

EP    0580928 A1    2/1994
EP    0650694 B1    7/1998
(Continued)

OTHER PUBLICATIONS

"Structure and Properties of Ceramics, 2018, The American Ceramic Society" (Year: 2018).*
"Advanced Ceramics, Nov. 3, 2016, Encyclopaedia Britannica Inc., Britannica Online Encyclopedia" (Year: 2016).*
(Continued)

*Primary Examiner* — Joseph M Dietrich
*Assistant Examiner* — Michael T. Holtzclaw
(74) *Attorney, Agent, or Firm* — Branch Partners PLLC; Bruce E. Black

(57) ABSTRACT

A connector assembly for an implantable device includes a feedthrough interface having a ceramic feedthrough and a ferrule attached to, and forming a perimeter around, the ceramic feedthrough; a lower contact housing coupled to the feedthrough interface, where the lower contact housing and ceramic feedthrough define wire holes extending therethrough; an upper contact housing attached to the lower contact housing and collectively defining contact receptacles, each of the contact receptacles defining an opening for at least one of the wire holes; connector contacts with each connector contact disposed in a one of the contact receptacles; and wires with each of the wires coupled to one of the connector contacts and extending through one of the wire holes so that the respective wire extends out of the ceramic feedthrough.

20 Claims, 11 Drawing Sheets

(51) Int. Cl.
*H01R 13/22* (2006.01)
*H01R 13/52* (2006.01)
*H01R 43/18* (2006.01)
*H01R 43/20* (2006.01)
*H05K 5/06* (2006.01)
*H01R 13/621* (2006.01)

(52) U.S. Cl.
CPC ......... *H01R 13/5208* (2013.01); *H01R 43/18* (2013.01); *H01R 43/20* (2013.01); *H05K 5/069* (2013.01); *A61N 1/36071* (2013.01); *H01R 13/621* (2013.01); *H01R 2201/12* (2013.01)

(58) Field of Classification Search
CPC .......... A61N 1/3605; A61N 1/36; A61N 1/18; A61N 1/36062; A61N 1/3606; A61N 1/36067; H01R 13/22; H01R 3/5208; H01R 43/18; H01R 43/20; H01R 13/621; H01R 2201/12; H05K 5/069
See application file for complete search history.

(56) References Cited

U.S. PATENT DOCUMENTS

| | | |
|---|---|---|
| 3,718,142 A | 2/1973 | Mulier |
| 3,757,789 A | 9/1973 | Shanker |
| 3,771,106 A | 11/1973 | Matsumoto et al. |
| 3,908,668 A | 9/1975 | Bolduc |
| 3,951,154 A | 4/1976 | Hartlaub |
| 3,990,727 A | 11/1976 | Gallagher |
| 4,003,616 A | 1/1977 | Springer |
| 4,112,953 A | 9/1978 | Shanker et al. |
| 4,142,532 A | 3/1979 | Ware |
| 4,180,078 A | 12/1979 | Anderson |
| 4,245,642 A | 1/1981 | Skubitz et al. |
| 4,259,962 A | 4/1981 | Peers-Treverton |
| 4,310,001 A | 1/1982 | Comben |
| 4,364,625 A | 12/1982 | Baker et al. |
| 4,367,907 A | 1/1983 | Buck |
| 4,411,276 A | 10/1983 | Dickhudt et al. |
| 4,411,277 A | 10/1983 | Dickhudt |
| 4,461,194 A | 7/1984 | Moore |
| 4,466,441 A | 8/1984 | Skubitz et al. |
| 4,516,820 A | 5/1985 | Kuzma |
| RE31,990 E | 9/1985 | Sluetz et al. |
| 4,540,236 A | 9/1985 | Peers-Trevarton |
| 4,602,624 A | 7/1986 | Naples et al. |
| 4,603,696 A | 8/1986 | Cross, Jr. et al. |
| 4,614,395 A | 9/1986 | Peers-Trevarton |
| 4,630,611 A | 12/1986 | King |
| 4,695,116 A | 9/1987 | Bailey et al. |
| 4,695,117 A | 9/1987 | Kysiak |
| 4,712,557 A | 12/1987 | Harris |
| 4,715,380 A | 12/1987 | Harris |
| 4,744,370 A | 5/1988 | Harris |
| 4,784,141 A | 11/1988 | Peers-Trevarton |
| 4,832,032 A | 5/1989 | Schneider |
| 4,840,580 A | 6/1989 | Saell et al. |
| 4,850,359 A | 7/1989 | Putz |
| 4,860,750 A | 8/1989 | Frey et al. |
| 4,867,708 A | 9/1989 | Iizuka |
| 4,869,255 A | 9/1989 | Putz |
| 4,898,173 A | 2/1990 | Dagiow et al. |
| 4,899,753 A | 2/1990 | Inoue et al. |
| 4,951,687 A | 8/1990 | Ufford et al. |
| 4,995,389 A | 2/1991 | Harris |
| 5,000,177 A | 3/1991 | Hoffman et al. |
| 5,000,194 A | 3/1991 | van den Honert et al. |
| 5,007,435 A | 4/1991 | Doan et al. |
| 5,007,864 A | 4/1991 | Stutz, Jr. |
| 5,070,605 A | 12/1991 | Daglow et al. |
| 5,082,453 A | 1/1992 | Stutz, Jr. |
| 5,086,773 A | 2/1992 | Ware |
| 5,135,001 A | 8/1992 | Sinofsky et al. |
| 5,193,539 A | 3/1993 | Schulman et al. |
| 5,193,540 A | 3/1993 | Schulman et al. |
| 5,201,865 A | 4/1993 | Kuehn |
| 5,241,957 A | 9/1993 | Camps et al. |
| 5,252,090 A | 10/1993 | Giurtino et al. |
| 5,261,395 A | 11/1993 | Oleen et al. |
| 5,312,439 A | 5/1994 | Loeb |
| 5,324,312 A | 6/1994 | Stokes et al. |
| 5,330,521 A | 7/1994 | Cohen |
| 5,336,246 A | 8/1994 | Dantanarayana |
| 5,348,481 A | 9/1994 | Ortiz |
| 5,354,326 A | 10/1994 | Comben et al. |
| 5,358,514 A | 10/1994 | Schulman et al. |
| 5,368,496 A | 11/1994 | Ranalletta et al. |
| 5,374,279 A | 12/1994 | Duffin, Jr. et al. |
| 5,374,285 A | 12/1994 | Vaiani et al. |
| 5,383,913 A | 1/1995 | Schiff |
| 5,413,595 A | 5/1995 | Stutz, Jr. |
| 5,433,734 A | 7/1995 | Stokes et al. |
| 5,435,731 A | 7/1995 | Kang |
| 5,458,629 A | 10/1995 | Baudino et al. |
| 5,486,202 A | 1/1996 | Bradshaw |
| 5,489,225 A | 2/1996 | Julian |
| 5,509,928 A | 4/1996 | Acken |
| 5,522,874 A | 6/1996 | Gates |
| 5,534,019 A | 7/1996 | Paspa |
| 5,545,188 A | 8/1996 | Bradshaw et al. |
| 5,545,189 A | 8/1996 | Fayram |
| 5,582,180 A | 8/1996 | Manset et al. |
| 5,560,358 A | 10/1996 | Arnold et al. |
| 5,679,026 A | 10/1997 | Fain et al. |
| 5,683,433 A | 11/1997 | Carson |
| 5,711,316 A | 1/1998 | Elsberry et al. |
| 5,713,922 A | 2/1998 | King |
| 5,720,631 A | 2/1998 | Carson et al. |
| 5,730,628 A | 3/1998 | Hawkins |
| 5,755,743 A | 5/1998 | Volz et al. |
| 5,766,042 A | 6/1998 | Ries et al. |
| 5,782,892 A | 7/1998 | Castle et al. |
| 5,796,044 A | 8/1998 | Cobian et al. |
| 5,800,350 A | 9/1998 | Coppleson et al. |
| 5,800,495 A | 9/1998 | Machek et al. |
| 5,807,144 A | 9/1998 | Sivard |
| 5,837,006 A | 11/1998 | Ocel et al. |
| 5,843,141 A | 12/1998 | Bischoff et al. |
| 5,843,148 A | 12/1998 | Gijsbers et al. |
| 5,906,634 A | 5/1999 | Flynn et al. |
| 5,931,861 A | 8/1999 | Werner et al. |
| 5,938,688 A | 8/1999 | Schiff |
| 5,951,595 A | 9/1999 | Moberg et al. |
| 5,968,082 A | 10/1999 | Heil |
| 5,987,361 A | 11/1999 | Mortimer |
| 5,989,077 A | 11/1999 | Mast et al. |
| 6,006,135 A | 12/1999 | Kast et al. |
| 6,018,684 A | 1/2000 | Bartig et al. |
| 6,038,479 A | 3/2000 | Werner et al. |
| 6,038,481 A | 3/2000 | Werner et al. |
| 6,042,432 A | 3/2000 | Hashazawa et al. |
| 6,051,017 A | 4/2000 | Loeb et al. |
| 6,080,188 A | 6/2000 | Rowley et al. |
| 6,112,120 A | 8/2000 | Correas |
| 6,112,121 A | 8/2000 | Paul et al. |
| 6,125,302 A | 9/2000 | Kuzma |
| 6,134,478 A | 10/2000 | Spehr |
| 6,154,678 A | 11/2000 | Lauro |
| 6,162,101 A | 12/2000 | Fischer et al. |
| 6,164,284 A | 12/2000 | Schulman et al. |
| 6,167,311 A | 12/2000 | King et al. |
| 6,167,314 A | 12/2000 | Fischer, Sr. et al. |
| 6,175,710 B1 | 1/2001 | Kamaji et al. |
| 6,181,969 B1 | 1/2001 | Gord |
| 6,185,452 B1 | 2/2001 | Schulman et al. |
| 6,192,278 B1 | 2/2001 | Werner et al. |
| 6,198,969 B1 | 3/2001 | Kuzma |
| 6,208,894 B1 | 3/2001 | Schulman et al. |
| 6,224,450 B1 | 5/2001 | Norton |
| 6,271,094 B1 | 8/2001 | Boyd et al. |
| 6,295,944 B1 | 10/2001 | Lovett |

(56) References Cited

U.S. PATENT DOCUMENTS

| | | |
|---|---|---|
| 6,319,021 B1 | 11/2001 | Biliman |
| 6,321,126 B1 | 11/2001 | Kuzma |
| 6,322,559 B1 | 11/2001 | Daulton et al. |
| 6,343,233 B1 | 1/2002 | Werner et al. |
| 6,364,278 B1 | 4/2002 | Lin et al. |
| 6,370,434 B1 | 4/2002 | Zhang et al. |
| 6,391,985 B1 | 5/2002 | Goode et al. |
| 6,397,108 B1 | 5/2002 | Camps et al. |
| 6,415,168 B1 | 7/2002 | Putz |
| 6,428,336 B1 | 8/2002 | Akerfeldt |
| 6,428,368 B1 | 8/2002 | Hawkins et al. |
| 6,430,442 B1 | 8/2002 | Peters et al. |
| 6,466,824 B1 | 10/2002 | Struble |
| 6,473,654 B1 | 10/2002 | Chinn |
| 6,498,952 B2 | 12/2002 | Imani et al. |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,604,283 B1 | 8/2003 | Kuzma |
| 6,605,094 B1 | 8/2003 | Mann et al. |
| 6,609,029 B1 | 8/2003 | Mann et al. |
| 6,609,032 B1 | 8/2003 | Woods et al. |
| 6,654,641 B1 | 11/2003 | Froberg |
| 6,662,035 B2 * | 12/2003 | Sochor ............ A61N 1/0529 439/909 |
| 6,663,570 B2 | 12/2003 | Mott |
| 6,671,534 B2 | 12/2003 | Putz |
| 6,671,553 B1 | 12/2003 | Helland et al. |
| 6,678,564 B2 | 1/2004 | Ketterl et al. |
| 6,725,096 B2 | 4/2004 | Chinn et al. |
| 6,741,892 B1 | 5/2004 | Meadows et al. |
| 6,757,039 B2 | 6/2004 | Ma |
| 6,757,970 B1 | 7/2004 | Kuzma et al. |
| 6,799,991 B2 | 10/2004 | Williams et al. |
| 6,805,675 B1 | 10/2004 | Gardeski et al. |
| 6,854,994 B2 | 2/2005 | Stein et al. |
| 6,878,013 B1 | 4/2005 | Behan |
| 6,895,276 B2 | 5/2005 | Kast et al. |
| 6,895,280 B2 | 5/2005 | Meadows et al. |
| 6,913,478 B2 | 7/2005 | Lamrey |
| 6,921,295 B2 | 7/2005 | Sommer et al. |
| 6,968,235 B2 | 11/2005 | Belden et al. |
| 6,980,863 B2 | 12/2005 | van Venrooij et al. |
| 7,027,852 B2 | 4/2006 | Helland |
| 7,047,084 B2 | 5/2006 | Erickson et al. |
| 7,058,452 B2 | 6/2006 | Dahlberg |
| 7,069,081 B2 | 6/2006 | Biggs et al. |
| 7,083,474 B1 | 8/2006 | Fleck et al. |
| 7,108,549 B2 | 9/2006 | Lyu et al. |
| 7,110,827 B2 | 9/2006 | Sage et al. |
| 7,128,600 B2 | 10/2006 | Osypka |
| 7,155,283 B2 | 12/2006 | Ries et al. |
| 7,164,951 B2 | 1/2007 | Ries et al. |
| 7,168,165 B2 | 1/2007 | Calzada et al. |
| 7,191,009 B2 | 3/2007 | Laske et al. |
| 7,195,523 B2 | 3/2007 | Naviaux |
| 7,203,548 B2 | 4/2007 | Whitehurst et al. |
| 7,225,034 B2 | 5/2007 | Ries et al. |
| 7,231,253 B2 | 6/2007 | Tidemand et al. |
| 7,241,180 B1 | 7/2007 | Rentas |
| 7,242,987 B2 | 7/2007 | Holleman et al. |
| 7,244,150 B1 | 7/2007 | Brase et al. |
| 7,270,568 B2 | 9/2007 | Osypka |
| 7,283,878 B2 | 10/2007 | Brostrom et al. |
| 7,286,882 B2 | 10/2007 | Cole |
| 7,287,995 B2 | 10/2007 | Stein et al. |
| 7,292,890 B2 | 11/2007 | Whitehurst et al. |
| 7,396,335 B2 | 7/2008 | Gardeski et al. |
| 7,402,083 B2 | 7/2008 | Kest et al. |
| 7,422,487 B2 | 9/2008 | Osypka |
| 7,430,958 B2 | 10/2008 | Wong |
| 7,437,193 B2 | 10/2008 | Parramon et al. |
| 7,450,997 B1 | 11/2008 | Pianca et al. |
| 7,489,971 B1 | 2/2009 | Franz |
| 7,510,447 B2 | 3/2009 | Drew |
| 7,512,446 B2 | 3/2009 | Honeck |
| 7,526,339 B2 | 4/2009 | Lahti et al. |
| 7,539,542 B1 | 5/2009 | Malinowski |
| 7,548,788 B2 | 6/2009 | Chinn et al. |
| 7,554,493 B1 | 6/2009 | Rahman |
| 7,583,999 B2 | 9/2009 | Bedenbaugh |
| 7,585,190 B2 | 9/2009 | Osypka |
| 7,590,451 B2 | 9/2009 | Tronnes et al. |
| 7,650,184 B2 | 1/2010 | Walter |
| 7,668,601 B2 | 2/2010 | Hegland et al. |
| 7,672,734 B2 | 3/2010 | Anderson et al. |
| 7,736,191 B1 | 6/2010 | Sochor |
| 7,758,384 B2 | 7/2010 | Alexander et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,798,864 B2 | 9/2010 | Barker et al. |
| 7,803,021 B1 | 9/2010 | Brase |
| 7,809,446 B2 | 10/2010 | Meadows |
| 7,822,477 B2 | 10/2010 | Rey et al. |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,046,073 B1 | 10/2011 | Pianca |
| 8,046,074 B2 | 10/2011 | Barker |
| 8,078,280 B2 | 12/2011 | Sage |
| 8,099,177 B2 | 1/2012 | Dahlberg |
| 8,100,726 B2 | 1/2012 | Harlan et al. |
| 8,140,163 B1 | 3/2012 | Daglow et al. |
| 8,162,684 B1 | 4/2012 | Sochor |
| 8,167,660 B2 | 5/2012 | Dilmaghanian et al. |
| 8,175,710 B2 | 5/2012 | He |
| 8,190,259 B1 | 5/2012 | Smith et al. |
| 8,206,180 B1 | 6/2012 | Kast et al. |
| 8,224,450 B2 | 7/2012 | Brase |
| 8,225,504 B2 | 7/2012 | Dye et al. |
| 8,239,042 B2 | 8/2012 | Chinn et al. |
| 8,267,708 B1 | 9/2012 | Sochor |
| 8,271,094 B1 | 9/2012 | Moffitt et al. |
| 8,295,944 B2 | 10/2012 | Howard et al. |
| 8,301,255 B2 | 10/2012 | Barker |
| 8,321,025 B2 | 11/2012 | Bedenbaugh |
| 8,342,887 B2 | 1/2013 | Gleason et al. |
| 8,359,107 B2 | 1/2013 | Pianca et al. |
| 8,364,278 B2 | 1/2013 | Pianca et al. |
| 8,391,985 B2 | 3/2013 | McDonald |
| 8,412,330 B2 | 4/2013 | Kast et al. |
| 8,527,054 B2 | 9/2013 | North |
| 8,548,582 B2 | 10/2013 | McDonald et al. |
| 8,583,237 B2 | 11/2013 | Bedenbaugh |
| 8,600,507 B2 | 12/2013 | Brase et al. |
| 8,682,439 B2 | 3/2014 | DeRohan et al. |
| 8,688,235 B1 | 4/2014 | Pianca et al. |
| 8,751,002 B2 | 6/2014 | Kest et al. |
| 8,784,143 B2 | 7/2014 | Edgell et al. |
| 8,831,742 B2 | 9/2014 | Pianca et al. |
| 8,849,396 B2 | 9/2014 | DeRohan et al. |
| 8,849,415 B2 | 9/2014 | Bedenbaugh |
| 8,897,876 B2 | 11/2014 | Sundaramurthy et al. |
| 8,897,891 B2 | 11/2014 | Romero |
| 8,968,331 B1 | 3/2015 | Sochor |
| 9,101,775 B2 | 8/2015 | Barker |
| 9,149,630 B2 | 10/2015 | Howard et al. |
| 9,162,048 B2 | 10/2015 | Romero et al. |
| 9,234,591 B2 | 1/2016 | Dilmaghanian et al. |
| 9,270,070 B2 | 2/2016 | Pianca |
| 9,289,596 B2 | 3/2016 | Leven |

(56) References Cited

U.S. PATENT DOCUMENTS

| | | |
|---|---|---|
| 9,352,147 B2 | 5/2016 | Nguyen-stella et al. |
| 9,381,348 B2 | 7/2016 | Romero et al. |
| 9,403,022 B2 | 8/2016 | Ries et al. |
| 9,409,032 B2 | 8/2016 | Brase et al. |
| 9,440,066 B2 | 9/2016 | Black |
| 9,498,618 B2 | 11/2016 | Stetson et al. |
| 9,498,620 B2 | 11/2016 | Romero et al. |
| 9,504,839 B2 | 11/2016 | Leven |
| 9,604,068 B2 | 3/2017 | Malinowski |
| 9,656,093 B2 | 5/2017 | Villarta et al. |
| 9,770,598 B2 | 9/2017 | Malinowski et al. |
| 9,855,413 B2 | 1/2018 | Vadlamudi et al. |
| 9,865,533 B2 * | 1/2018 | Ruben .................. A61N 1/3754 |
| 10,342,983 B2 * | 7/2019 | Nageri .................. A61B 5/6868 |
| 2001/0023368 A1 | 9/2001 | Black et al. |
| 2002/0143376 A1 | 10/2002 | Chinn et al. |
| 2002/0156513 A1 | 10/2002 | Borkan |
| 2002/0183817 A1 | 12/2002 | Van Venrooij et al. |
| 2003/0163171 A1 | 8/2003 | Kast et al. |
| 2004/0064164 A1 | 4/2004 | Ries et al. |
| 2004/0230268 A1 | 11/2004 | Huff et al. |
| 2004/0260373 A1 | 12/2004 | Ries et al. |
| 2005/0015130 A1 | 1/2005 | Gill |
| 2005/0027326 A1 | 2/2005 | Ries et al. |
| 2005/0027327 A1 | 2/2005 | Ries et al. |
| 2005/0038489 A1 | 2/2005 | Grill |
| 2005/0043770 A1 | 2/2005 | Hine et al. |
| 2005/0043771 A1 | 2/2005 | Sommer et al. |
| 2005/0137665 A1 | 6/2005 | Cole |
| 2005/0171587 A1 | 8/2005 | Daglow et al. |
| 2005/0186829 A1 | 8/2005 | Balsells |
| 2005/0272280 A1 | 12/2005 | Osypka |
| 2006/0015163 A1 | 1/2006 | Brown |
| 2006/0025841 A1 | 2/2006 | McIntyre |
| 2006/0030918 A1 | 2/2006 | Chinn |
| 2006/0167522 A1 | 7/2006 | Malinowski |
| 2006/0224208 A1 | 10/2006 | Naviaux |
| 2006/0247697 A1 | 11/2006 | Sharma et al. |
| 2006/0247749 A1 | 11/2006 | Colvin |
| 2006/0259106 A1 | 11/2006 | Arnholdt et al. |
| 2007/0042648 A1 | 2/2007 | Balsells |
| 2007/0142889 A1 | 6/2007 | Whitehurst et al. |
| 2007/0150036 A1 | 6/2007 | Anderson |
| 2007/0161294 A1 | 7/2007 | Brase et al. |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0139031 A1 | 6/2008 | Ries et al. |
| 2008/0177167 A1 | 7/2008 | Janzig et al. |
| 2008/0208277 A1 | 8/2008 | Janzig et al. |
| 2008/0208278 A1 | 8/2008 | Janzig et al. |
| 2008/0208279 A1 | 8/2008 | Janzig et al. |
| 2008/0215125 A1 | 9/2008 | Farah et al. |
| 2008/0255647 A1 | 10/2008 | Jensen et al. |
| 2008/0274651 A1 | 11/2008 | Boyd et al. |
| 2009/0054941 A1 | 2/2009 | Eggen et al. |
| 2009/0187222 A1 | 7/2009 | Barker |
| 2009/0204192 A1 | 8/2009 | Carlton et al. |
| 2009/0264943 A1 | 10/2009 | Barker |
| 2009/0276021 A1 | 11/2009 | Meadows et al. |
| 2009/0287191 A1 | 11/2009 | Ferren et al. |
| 2010/0029127 A1 | 2/2010 | Sjostedt |
| 2010/0030298 A1 | 2/2010 | Martens et al. |
| 2010/0036468 A1 | 2/2010 | Deere-et al. |
| 2010/0057176 A1 | 3/2010 | Barker |
| 2010/0070012 A1 | 3/2010 | Chinn et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0022100 A1 | 1/2011 | Brase et al. |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0184480 A1 | 7/2011 | Kast et al. |
| 2011/0238129 A1 | 9/2011 | Moffitt et al. |
| 2011/0245903 A1 | 10/2011 | Schulte et al. |
| 2011/0270330 A1 | 11/2011 | Janzig et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0053646 A1 | 3/2012 | Brase et al. |
| 2012/0071937 A1 | 3/2012 | Sundaramurthy et al. |
| 2012/0071949 A1 | 3/2012 | Pianca et al. |
| 2012/0165911 A1 | 6/2012 | Pianca |
| 2012/0185019 A1 | 7/2012 | Schramm et al. |
| 2012/0197375 A1 | 8/2012 | Pianca et al. |
| 2012/0203302 A1 | 8/2012 | Moffit et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232603 A1 | 9/2012 | Sage |
| 2012/0253443 A1 | 10/2012 | Dilmaghanian et al. |
| 2012/0259386 A1 | 10/2012 | DeRohan et al. |
| 2012/0316615 A1 | 12/2012 | DiGiore et al. |
| 2013/0035732 A1 | 2/2013 | Miltich et al. |
| 2013/0053864 A1 | 2/2013 | Geroy et al. |
| 2013/0098678 A1 | 4/2013 | Barker |
| 2013/0105071 A1 | 5/2013 | DiGiore et al. |
| 2013/0109254 A1 | 5/2013 | Klardie et al. |
| 2013/0116754 A1 | 5/2013 | Sharma et al. |
| 2013/0149031 A1 | 6/2013 | Changsrivong et al. |
| 2013/0197424 A1 | 8/2013 | Bedenbaugh |
| 2013/0197602 A1 | 8/2013 | Pianca et al. |
| 2013/0197603 A1 | 8/2013 | Eiger |
| 2013/0218154 A1 | 8/2013 | Carbunaru |
| 2013/0261684 A1 | 10/2013 | Howard |
| 2013/0288501 A1 | 10/2013 | Russell et al. |
| 2013/0304140 A1 | 11/2013 | Derohan et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0148885 A1 | 5/2014 | DeRohan et al. |
| 2014/0180375 A1 | 6/2014 | Pianca et al. |
| 2014/0214130 A1 * | 7/2014 | Lopez .................. A61N 1/3754 607/59 |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0025609 A1 | 1/2015 | Govea |
| 2015/0045864 A1 | 2/2015 | Howard |
| 2015/0066120 A1 | 3/2015 | Govea |
| 2015/0119965 A1 | 4/2015 | Govea |
| 2015/0151113 A1 | 6/2015 | Govea et al. |
| 2015/0209575 A1 | 7/2015 | Black |
| 2015/0360023 A1 | 12/2015 | Howard et al. |
| 2015/0374978 A1 | 12/2015 | Howard et al. |
| 2016/0059019 A1 | 3/2016 | Malinowski et al. |
| 2016/0129242 A1 | 5/2016 | Malinowski |
| 2016/0129265 A1 | 5/2016 | Malinowski |
| 2016/0158558 A1 | 6/2016 | Shanahan et al. |

(56) References Cited

U.S. PATENT DOCUMENTS

| | | |
|---|---|---|
| 2016/0206891 A1 | 7/2016 | Howard et al. |
| 2016/0228692 A1 | 8/2016 | Steinke et al. |
| 2016/0263384 A1 | 9/2016 | Stevenson et al. |
| 2016/0296745 A1 | 10/2016 | Govea et al. |
| 2016/0375238 A1 | 12/2016 | Leven et al. |
| 2017/0072187 A1 | 3/2017 | Howard et al. |
| 2017/0143978 A1 | 5/2017 | Barker |
| 2017/0203104 A1 | 7/2017 | Nageri et al. |
| 2017/0361108 A1 | 12/2017 | Leven |
| 2018/0008832 A1 | 1/2018 | Leven |
| 2018/0028820 A1 | 2/2018 | Nageri |
| 2018/0093098 A1 | 4/2018 | Nageri et al. |
| 2018/0126175 A1 | 5/2018 | Seitz et al. |
| 2018/0214687 A1 | 8/2018 | Nageri et al. |
| 2018/0243570 A1 | 8/2018 | Malinowski et al. |
| 2018/0289968 A1 | 10/2018 | Lopez |
| 2018/0369596 A1 | 12/2018 | Funderburk |
| 2019/0030345 A1 | 1/2019 | Funderburk |
| 2019/0083793 A1 | 3/2019 | Nageri |
| 2019/0083794 A1 | 3/2019 | Nageri |
| 2019/0103696 A1 | 4/2019 | Conger |
| 2019/0192861 A1 | 6/2019 | Lopez et al. |
| 2019/0217103 A1 | 7/2019 | Lopez |

FOREIGN PATENT DOCUMENTS

| | | |
|---|---|---|
| EP | 0832667 B1 | 2/2004 |
| EP | 1181947 B1 | 1/2006 |
| EP | 1625875 | 2/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |

OTHER PUBLICATIONS

International Search Report and Written Opinion for PCT Application No. PCT/US2019/031108 dated Sep. 6, 2019.

* cited by examiner

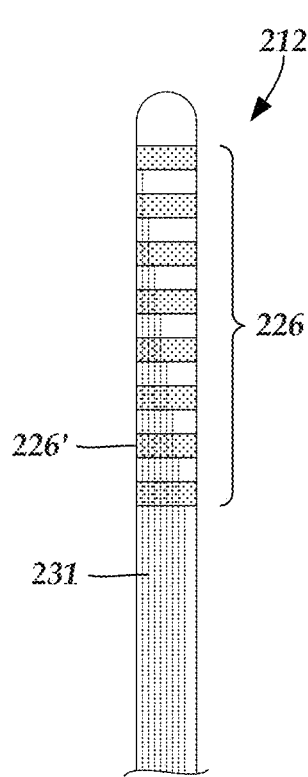
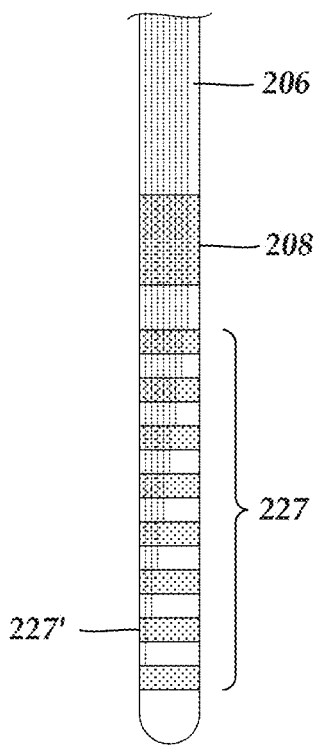
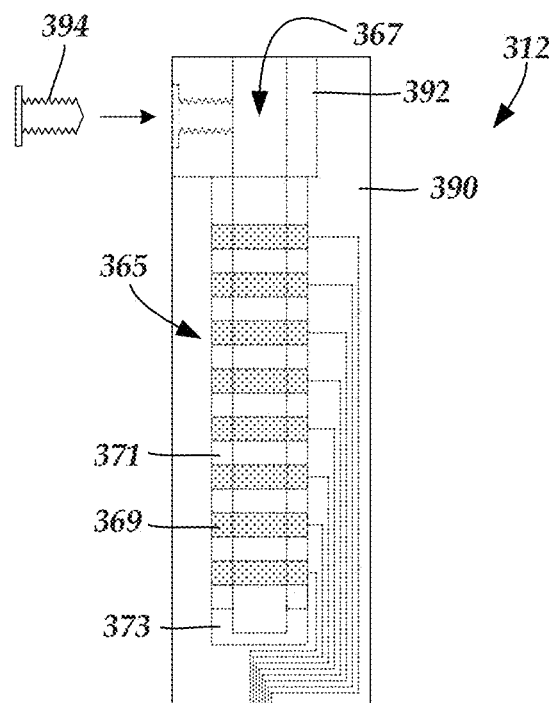
Fig. 2
Fig. 3

CONNECTOR ASSEMBLY FOR AN ELECTRICAL STIMULATION SYSTEM AND METHODS OF MAKING AND USING

CROSS-REFERENCE TO RELATED APPLICATIONS

This application claims the benefit under 35 U.S.C. § 119(e) of U.S. Provisional Patent Application Ser. No. 62/670,412, filed May 11, 2018, which is incorporated herein by reference.

FIELD

The present disclosure is directed to the area of implantable electrical stimulation systems and methods of making and using the systems. The present disclosure is also directed to a connector assembly for an electrical stimulation system, as well as the system and methods for making and using the connector.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator) and one or more stimulator electrodes. The one or more stimulator electrodes can be disposed along one or more leads, or along the control module, or both. The stimulator electrodes are in contact with or near the nerves, muscles, or other tissue to be stimulated. The pulse generator in the control module generates electrical pulses that are delivered by the electrodes to body tissue.

BRIEF SUMMARY

One aspect is a connector assembly for an implantable device. The connector assembly includes a feedthrough interface having a ceramic feedthrough and a ferrule attached to, and forming a perimeter around, the ceramic feedthrough; a lower contact housing coupled to the feedthrough interface, where the lower contact housing and ceramic feedthrough define wire holes extending therethrough; an upper contact housing attached to the lower contact housing, the upper and lower contact housings collectively defining contact receptacles and defining at least one lead receiving lumen extending through multiple ones of the contact receptacles to receive a portion of lead or lead extension inserted into the respective lead receiving lumen, each of the contact receptacles defining an opening for at least one of the wire holes; connector contacts with each connector contact disposed in a one of the contact receptacles and defining a lead receiving opening that is aligned with one of the at least one lead receiving lumen; and wires with each of the wires coupled to one of the connector contacts and extending through one of the wire holes so that the respective wire extends out of the ceramic feedthrough.

In at least some aspects, the lower contact housing is made of ceramic. In at least some aspects, the lower contact housing and ceramic feedthrough are a single molded ceramic piece. In at least some aspects, the wires are brazed to the ceramic feedthrough. In at least some aspects, the wires are brazed to the lower contact housing.

In at least some aspects, the ferrule is attached to the ceramic feedthrough by brazing. In at least some aspects, the upper contact housing includes a polymer or ceramic material. In at least some aspects, the connector assembly further includes a non-conductive connector housing disposed over or molded over the upper and lower contact housings.

In at least some aspects, each of the wires is directly attached to one of the connector contacts. In at least some aspects, the connector assembly further includes spacers with each spacer disposed between a pair of the contact receptacles. In at least some aspects, the connector assembly further includes adhesive coupling the upper contact housing to the lower contact housing.

Another aspect is an implantable control module for an electrical stimulation system. The control module includes any of the connector assemblies described above; a housing attached to the feedthrough interface of the connector assembly; and an electronic subassembly disposed in the housing and electrically coupled to the wires extending of the ceramic feedthrough.

In at least some aspects, the ferrule of the connector assembly is welded to the housing. In at least some aspects, the housing and the feedthrough interface form a hermetically sealed cavity within which the electronic subassembly is disposed.

Another aspect is an electrical stimulation system that includes any of the implantable control modules described above and an electrical stimulation lead having a proximal portion, a distal portion, terminals disposed along the proximal portion, electrodes disposed along the distal portion, and conductors electrically coupling the terminals to the electrodes, wherein the proximal portion of the electrical stimulation lead is configured for insertion into the connector assembly of the implantable control module.

In at least some aspects, the electrical stimulation system further includes a lead extension including a proximal portion, a distal portion, terminals disposed along the proximal portion, a connector disposed along the distal portion, connector contacts disposed within the connector, and conductors electrically coupling the terminals to the connector contacts, wherein the proximal portion of the electrical stimulation lead is configured for insertion into the connector of the lead extension and the proximal portion of the stimulation lead extension is configured for insertion into the connector assembly of the implantable control module.

A further aspect is a method of making a connector assembly. The method includes forming a ceramic feedthrough and a lower contact housing with contact receptacles in the lower contact housing and wire holes with each of the wire holes extending from a contact receptacle through the lower contact housing to an opening on an opposite side of the ceramic feedthrough; coupling a ferrule to a ceramic feedthrough; coupling one of a plurality of wires to each of a plurality of contacts; inserting each of the contacts into a different one of the contact receptacles and, for each of the contacts, inserting the wire coupled to the contact into the wire hole extending from with contact receptacle; and attaching an upper contact housing to the lower contact housing to hold the contacts within the contact receptacles.

In at least some aspects, forming the ceramic feedthrough and the lower contact housing includes molding the ceramic feedthrough and lower contact housing together. In at least some aspects, the method further includes inserting spacers between pairs of the contact receptacles. In at least some aspects, coupling ferrule to the ceramic feedthrough includes brazing the ferrule and wires to the ceramic feedthrough.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 2 is a schematic side view of one embodiment of an electrical stimulation lead;

FIG. 3 is a schematic side view of one embodiment of a lead extension suitable for coupling with the electrical stimulation lead of FIG. 2;

DETAILED DESCRIPTION

The present disclosure is directed to the area of implantable electrical stimulation systems and methods of making and using the systems. The present disclosure is also directed to a connector assembly for an electrical stimulation system, as well the system and methods for making and using the connector.

Suitable implantable electrical stimulation systems include, but are not limited to, a least one lead with one or more electrodes disposed on a distal portion of the lead and one or more terminals disposed on one or more proximal portions of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734;7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

A percutaneous lead for electrical stimulation (for example, deep brain, spinal cord, peripheral nerve, or cardiac-tissue stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. For illustrative purposes, the leads are described herein relative to use for deep brain stimulation, but it will be understood that any of the leads can be used for applications other than deep brain stimulation, including spinal cord stimulation, peripheral nerve stimulation, dorsal root ganglion stimulation, sacral nerve stimulation, or stimulation of other nerves, muscles, and tissues.

Figure 1:
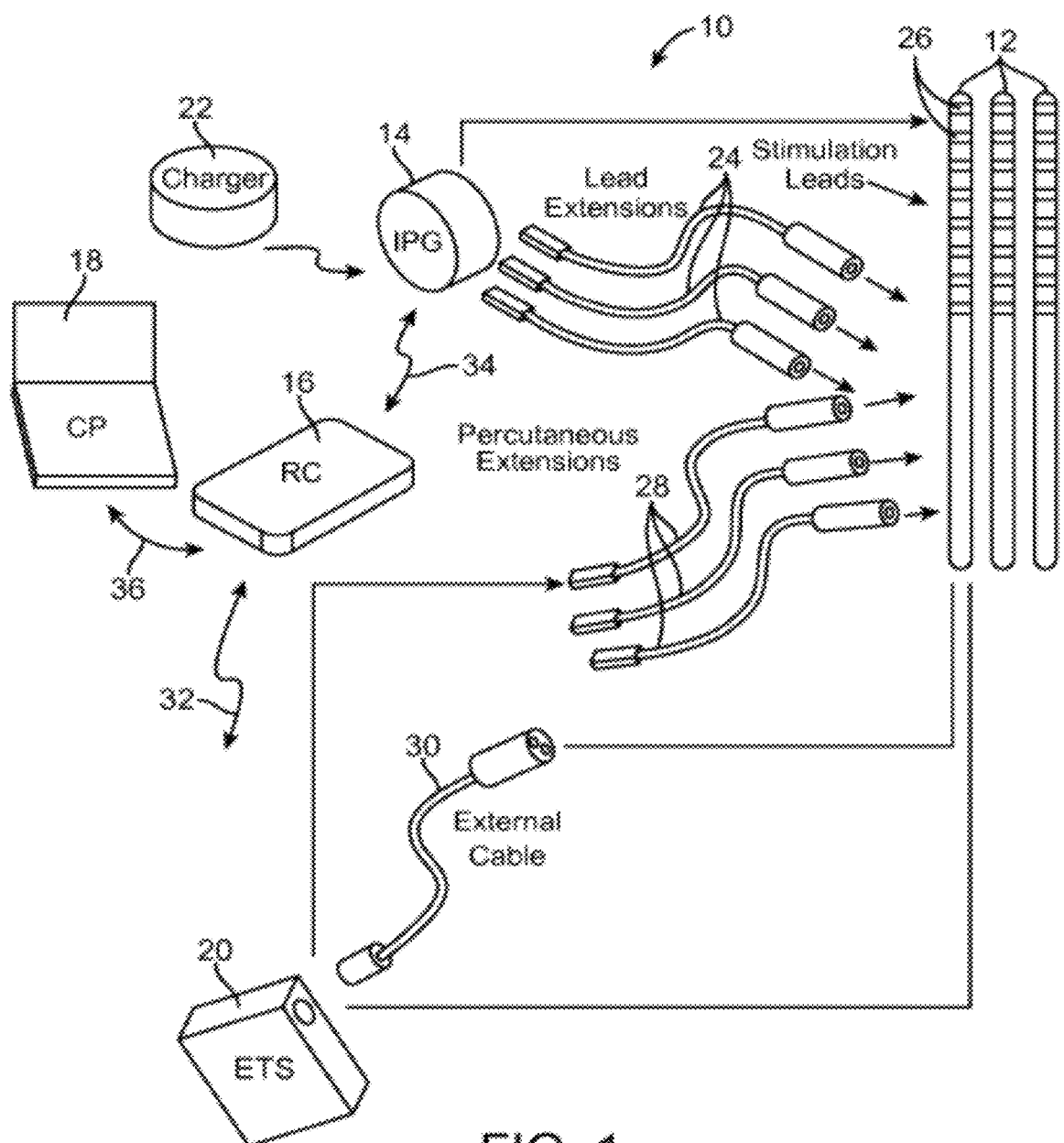
FIG. 1 is a schematic view of one embodiment of an electrical stimulation system.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally, via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator 14 can be implanted into a patient's body, for example, below the patient's clavicle area or within the patient's buttocks or abdominal cavity. The implantable pulse generator 14 can have eight stimulation channels which may be independently programmable to control the magnitude of the current stimulus from each channel. In some embodiments, the implantable pulse generator 14 can have more or fewer than eight stimulation channels (e.g., 4-, 6-, 16-, 32-, or more stimulation channels). The implantable pulse generator 14 can have one, two, three, four, or more connector ports, for receiving the terminals of the leads 12 and/or lead extensions 24.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Turning to FIG. 2, one or more leads are configured for coupling with a control module. The term "control module" is used herein to describe a pulse generator (e.g., the IPG 14 or the ETS 20 of FIG. 1). Stimulation signals generated by the control module are emitted by electrodes of the lead(s) to stimulate patient tissue. The electrodes of the lead(s) are electrically coupled to terminals of the lead(s) that, in turn, are electrically coupleable with the control module. In some embodiments, the lead(s) couple(s) directly with the control module. In other embodiments, one or more intermediary devices (e.g., a lead extension, an adaptor, a splitter, or the like) are disposed between the lead(s) and the control module.

Percutaneous leads are described herein for clarity of illustration. It will be understood that paddle leads and cuff leads can be used in lieu of, or in addition to, percutaneous leads. The leads described herein include 8 electrodes (+1 auxiliary electrode in some embodiments). It will be understood that the leads could include any suitable number of electrodes. The leads described herein exclusively include ring electrodes. It will be understood that the leads can include a distal-tip electrode, or one or more segmented electrodes in lieu of, or in addition to one or more ring electrodes. Additionally, the term "elongated member" used herein includes leads (e.g., percutaneous, paddle, cuff, or the like), as well as intermediary devices (e.g., lead extensions, adaptors, splitters, or the like).

FIG. 2 shows, in schematic side view, one embodiment of a lead 212 suitable for implanting into a patient and providing electrical stimulation. In some embodiments, the lead 212 is coupled directly to a control module. In other embodiments, the lead 212 is coupled to the control module via one or more intermediary devices. In the illustrated embodiment, an array of electrodes 226, which includes electrode 226', is disposed along a distal portion of a lead body 206 and an array of lead terminals 227, which includes lead terminal 227', is disposed along a proximal portion of the lead body. Lead conductors, such as lead conductor 231, extend along a longitudinal length of the lead 212 and electrically couple the array of electrodes 226 to the array lead terminals 227.

Conductors can extend along the longitudinal length of the lead 212 within one or more lumens defined in the lead. In other instances, the conductors may extend along the lead 212 within the lead body itself. The lead 212 includes an auxiliary terminal 208 disposed along the proximal portion of the body 206 to facilitate coupling of the proximal portion of the lead to a connector. The connector may be disposed along a control module. Alternatively, the auxiliary terminal 208 can be used to facilitate coupling of the proximal portion of the lead to a connector of an intermediary device, such as a lead extension which, in turn, is coupled to a connector of a control module.

FIG. 3 shows, in schematic side view, one embodiment of a lead extension 312 suitable for implanting into a patient and coupling a lead, such as the lead 212, to a control module. The lead extension 312 includes a lead-extension body 306 having a distal portion and a proximal portion. A lead-extension connector 390 is disposed along the distal portion of the lead-extension body 306 and an array of lead-extension terminals 327, such as lead-extension terminal 327', are disposed along the proximal portion of the lead-extension body 306.

The lead-extension connector 390 contains a lead-extension connector stack 365 that defines a connector lumen 367 configured to receive the proximal portion of an elongated member (e.g., lead 212). The lead-extension connector stack 365 includes lead-extension connector contacts, such as lead-extension connector contact 369, arranged along the connector lumen 367 and configured to electrically couple with terminals of the elongated member (e.g., lead 212) when the proximal portion of the elongated member is received by the lead-extension connector 390. The connector contacts can be electrically isolated from one another by electrically-nonconductive spacers, such as spacer 371. The connector stack may also include an end stop 373 to promote alignment of the elongated-member terminals with the lead-extension connector contacts.

The lead-extension connector 390 further includes a retention assembly for facilitating retention of the proximal portion of the elongated member (e.g., lead 212) when the proximal portion of the elongated member is received by the lead-extension connector 390. In the illustrated embodiment, the retention assembly includes a lead-extension retention block 392. The lead-extension retention block 392 is positioned to align with the auxiliary terminal (208 in FIG. 2) of the elongated member when the elongated member is received by the lead-extension connector 390. In the illustrated embodiment, the retention assembly further includes a retaining member (e.g., a set screw, a pin, or the like) 394 for pressing the auxiliary terminal of the inserted elongated member against the retention block to retain inserted elongated member within the lead-extension connector 390.

Lead-extension conductors, such as lead-extension conductor 331, extend along a longitudinal length of the lead extension 312 and electrically couple the lead-extension connector contacts to the array of lead-extension terminals 327. The lead-extension conductors can extend along the longitudinal length of the lead-extension body 306 within one or more lumens defined in the lead extension. In other instances, the lead-extension conductors may extend along the lead extension 312 within the lead-extension body 306 itself. The lead extension 312 includes an auxiliary terminal 308 disposed along the proximal portion of the lead-extension body 306 to facilitate coupling of the proximal portion of the lead extension to a connector, such as a control-module connector, another lead-extension connector, or the like.

Figure 4:
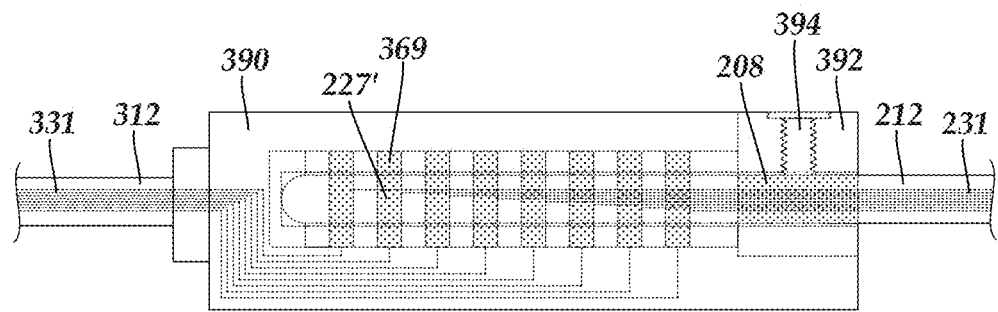
FIG. 4 is a schematic side view of one embodiment of the lead of FIG. 2 coupled to the lead extension of FIG. 3.

FIG. 4 shows, in schematic side view, one embodiment of the lead 212 received by the lead-extension connector 390. In the illustrated embodiment, the lead terminals, such as lead terminal 227', are aligned with the lead-extension connector contacts, such as lead-extension connector contact 369. Accordingly, the lead conductors 231 are electrically coupled with the lead-extension conductors 331. Additionally, in the illustrated embodiment the lead auxiliary terminal 208 is aligned with the lead-extension retention block 392 and the retaining member 394 is pressing the lead auxiliary terminal 208 against the lead-extension retention block to retain the lead 212 within the lead-extension connector 390.

Figure 5:
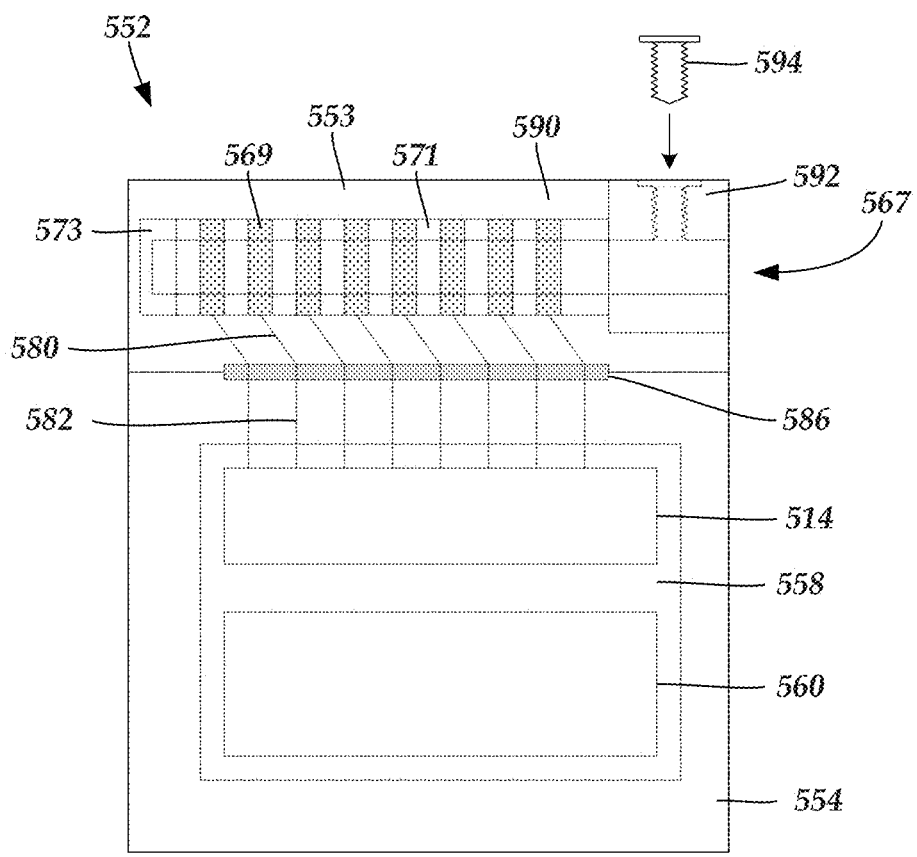
FIG. 5 is a schematic side view of one embodiment of a control module suitable for receiving either the lead of FIG. 2 or the lead extension of FIG. 3.

FIG. 5 shows, in schematic cross-sectional side view, a control module 552 suitable for coupling with an elongated member (e.g., the lead 212, the lead extension 312, or other intermediary device). The control module 552 includes a header 553 disposed along an outer surface of a sealed housing 554 that contains an electronic subassembly 558 with a pulse generator 514 and, optionally, a power supply 560.

A connector assembly 590 is disposed in the header 553. The connector assembly 590 is configured to receive an elongated device (e.g., the lead 212, the lead extension 312, or other intermediary device). The connector assembly 590 defines a connector lumen 567 configured to receive the proximal portion of the elongated member. An array of connector contacts, such as connector contact 569, is arranged along the connector lumen 567 and configured to electrically couple with terminals of the elongated member when the proximal portion of the elongated member is received by the connector 590. The connector contacts can be electrically isolated from one another by electrically-nonconductive spacers, such as spacer 571. The connector stack may also include an end stop 573 to promote alignment of the elongated-member terminals with the connector contacts.

Wires or contacts, such as wire 582, are electrically coupled to the electrical subassembly 558 and extend within the sealed housing 554 to a feedthrough interface 586 disposed along an interface between the header 553 and the sealed housing 554. The connector contacts are electrically coupled to interconnect conductors, such as wire 580, that extend along the header 553 and electrically couple the connector contacts to the wires 582 (and possibly feedthrough pins) at the feedthrough interface 586. In some embodiments, the header 553 is positioned over the feedthrough interface 586.

The connector assembly 590, optionally, includes a retention assembly for facilitating retention of the proximal portion of the elongated member when the proximal portion of the elongated member is received by the control module 552. In the illustrated embodiment, the retention assembly includes a retention block 592. The retention block 592 is positioned to align with a retention sleeve (see e.g., 608 in FIG. 6) of the elongated member when the elongated member is received by the connector assembly 590. In the illustrated embodiment, the retention assembly further includes a retaining member (e.g., a set screw, a pin, or the like) 594 for pressing the retention sleeve of the inserted elongated member against the retention block 592 to retain inserted elongated member within the connector assembly 590.

Figure 6:
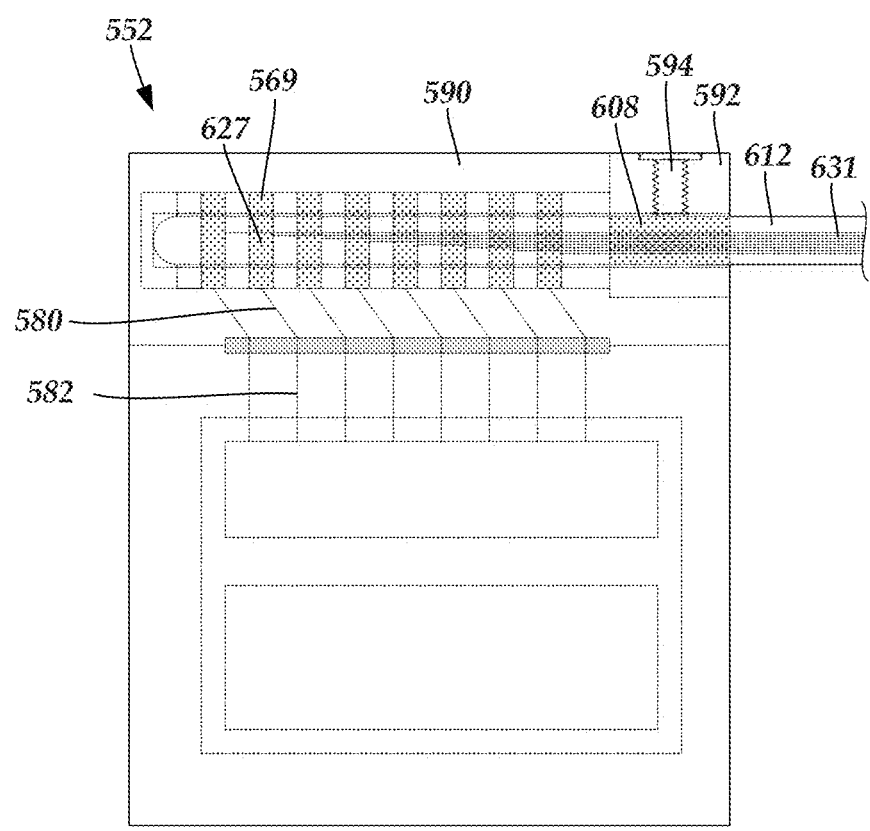
FIG. 6 is a schematic side view of one embodiment of an elongated member retained by the control module of FIG. 5.

FIG. 6 shows, in schematic side view, one embodiment of an elongated member 612 (e.g., the lead 212, the lead extension 312, or other intermediary device) received by the connector assembly 590 of the control module 552. In the illustrated embodiment, the elongated-member terminals, such as elongated-member terminal 627, are aligned with the connector contacts, such as connector contact 569. Accordingly, the elongated-member conductors 631 are electrically coupled with the interconnect conductors 580 and feedthrough interconnects 582. Additionally, in the illustrated embodiment a retention sleeve 608 disposed along the elongated member 612 is aligned with the retention block 592 and the retaining member 594 is pressing the retention sleeve 608 against the retention block 592 to retain the elongated member 612 within the connector assembly 590.

A connector assembly for an IPG (or other device) is often disposed within a header attached to a sealed housing containing an electronic subassembly (e.g., the IPG) with a feedthrough interconnect between the header and the sealed housing. Many conventional feedthrough interconnects and headers are complex and expensive due to the many processes and components that are used.

This disclosure presents arrangements and methods that, in at least some embodiments, can combine or eliminate some of the expensive components such as the contact housings and connector stack. In at least some embodiments, the arrangements and methods may reduce or eliminate some of the difficult assembly processes, such as a pin bending process allowing for a Z-axis assembly, or may be less prone to damage during assembly. In at least some embodiments, the arrangements and methods may reduce electrical impedance by eliminating the contact housing as an electrical path. In at least some embodiments, the arrangements and methods may facilitate self-alignment or simpler alignment of the contacts. In at least some embodiments, the arrangements and methods may have a lower profile than conventional connector assemblies. In at least some embodiments, the arrangements and methods may have lower resistance to insertion of the proximal end of the lead or lead extension.

Figure 7:
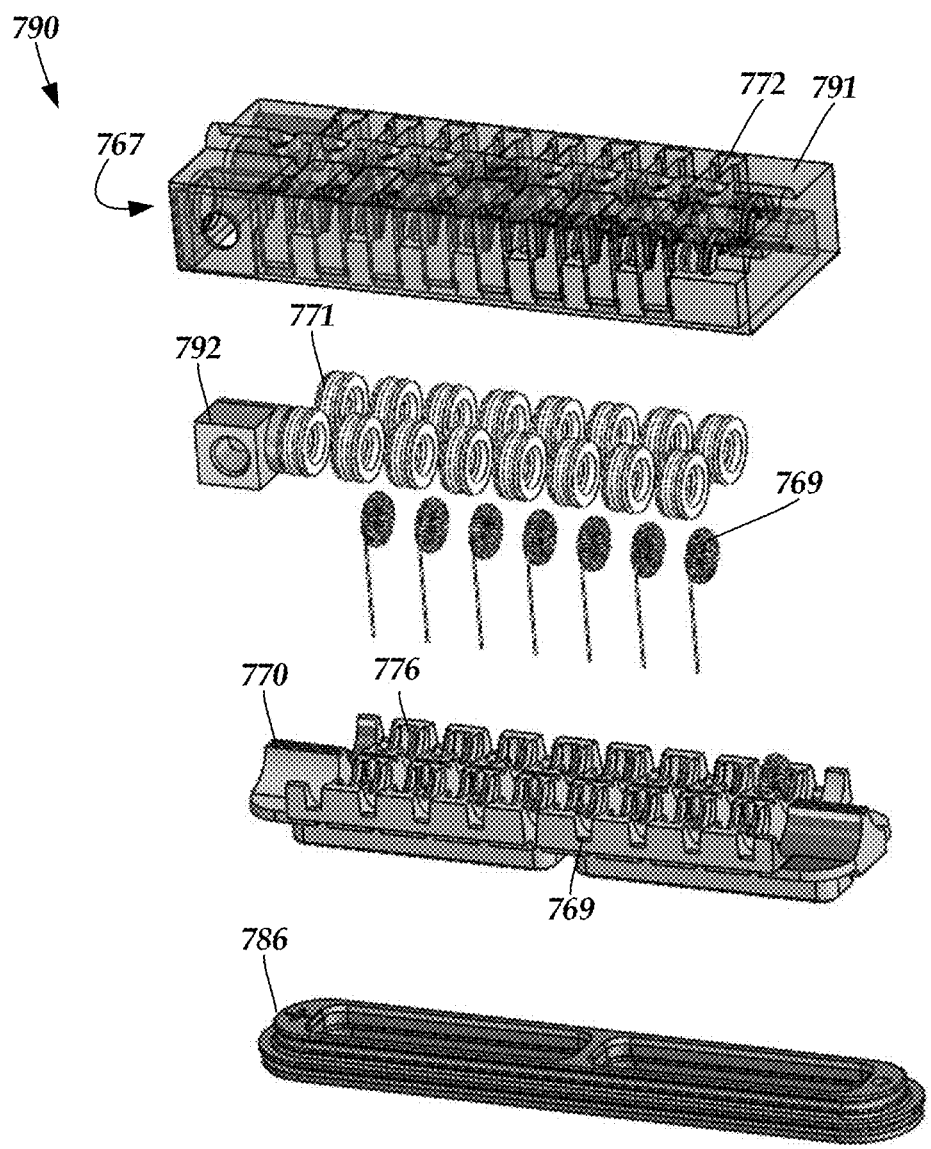
FIG. 7 is a schematic partially exploded view of one embodiment of a connector assembly.

FIG. 7 is a partially exploded view of components of a connector assembly 790 that includes a feedthrough interface 786, a lower contact housing 770, contacts 769, spacers 771, a retention block 792, an upper contact housing 772, and an optional connector housing 791 disposed over the remainder of the connector assembly 790. The upper and lower contact housing 772, 770, contacts 769, and spacers 771 define one or more connector lumens 767 that receive the proximal end of a lead or lead extension.

Figure 8A:
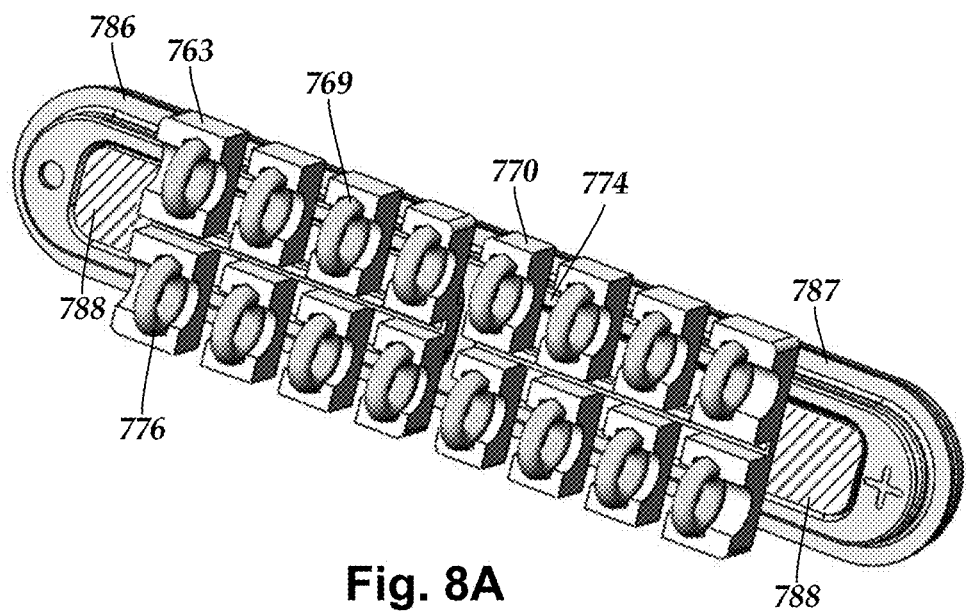
FIG. 8A is a schematic top view of one embodiment of a feedthrough interface, lower contact housing and contacts for a connector assembly.
Figure 8B:
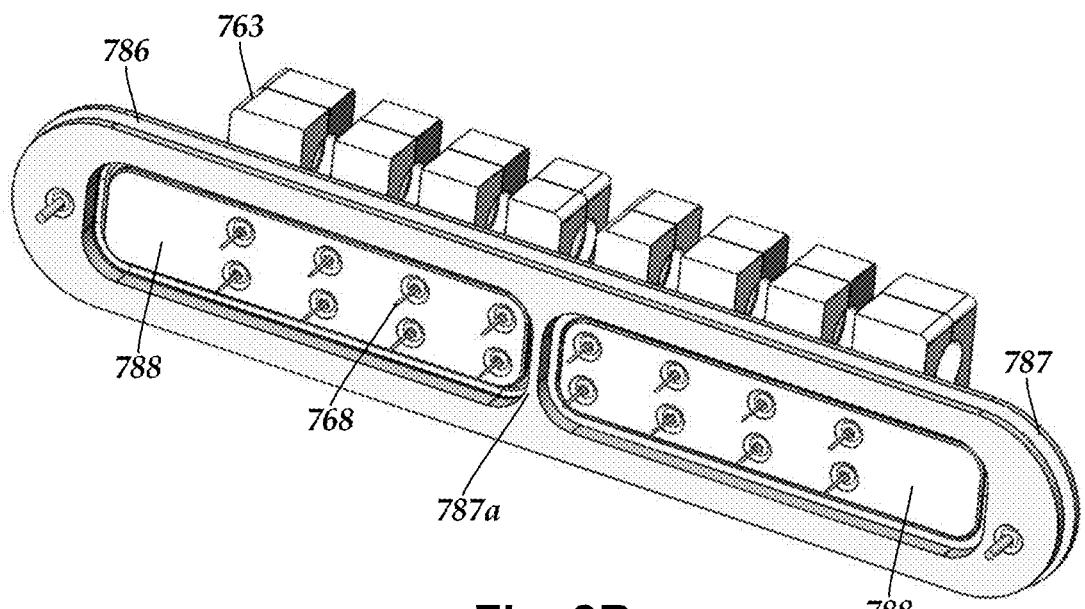
FIG. 8B is a schematic bottom view of one embodiment of a feedthrough interface, lower contact housing, upper contact housing, and wires.

As illustrated in FIGS. 8A and 8B, the feedthrough interface 786 includes a ferrule 787 and a ceramic feedthrough 788. FIG. 8A is a top view of the feedthrough interface 786 and illustrates other components such as contact receptacles 763 and contacts 769 disposed on the feedthrough interface. FIGS. 8B is a bottom view of a portion of the feedthrough interface 786 with additional components attached such as the contact receptacles 763 and wires 768. The wires 768 (FIG. 8B) extend from the contacts 769 through the ceramic feedthrough 788 and, during assembly, can be attached to contacts or wires of, or from, the electronic subassembly 558 (FIG. 5) in the sealed housing 554 (FIG. 5).

The ferrule 787 is made of metal and, at least in some embodiments, is welded to the sealed housing 554 (FIG. 5) during assembly of the device. The ferrule 787 can be made of any suitable metal including, but not limited to, titanium, titanium alloy, or the like. In at least some embodiments, the ferrule 787 forms a perimeter around the ceramic feedthrough 788. In at least some embodiments, the ferrule 787 may include at least one cross-bar 787a that separates at least a portion of the ceramic feedthrough 788 into two or more regions, as illustrated in FIG. 8B.

The ceramic feedthrough 788 electrically isolates the wires 768 from each other and is preferably brazed or otherwise attached to the ferrule 787. Any suitable braze can be used and may depend upon the materials of the ferrule 787 and the ceramic feedthrough 788. As an example, example, a gold braze may be used for a titanium ferrule and an aluminum oxide ceramic feedthrough. In at least some embodiments, the wires 768 are also brazed to the ceramic feedthrough 788. In at least some embodiments, the welding of the ferrule 787 to the sealed housing 554 (FIG. 5) and the brazing of the ceramic feedthrough 788 and wires 768 to the ferrule result in a hermetic seal between the feedthrough interface 786 and the sealed housing 554.

Any suitable ceramic can be used for the ceramic feedthrough 788 including, but not limited to, aluminum oxide or the like. Any suitable method can be used for forming the ceramic feedthrough 788 including, but not limited to, molding, such as injection molding, or the like.

Figure 9A:
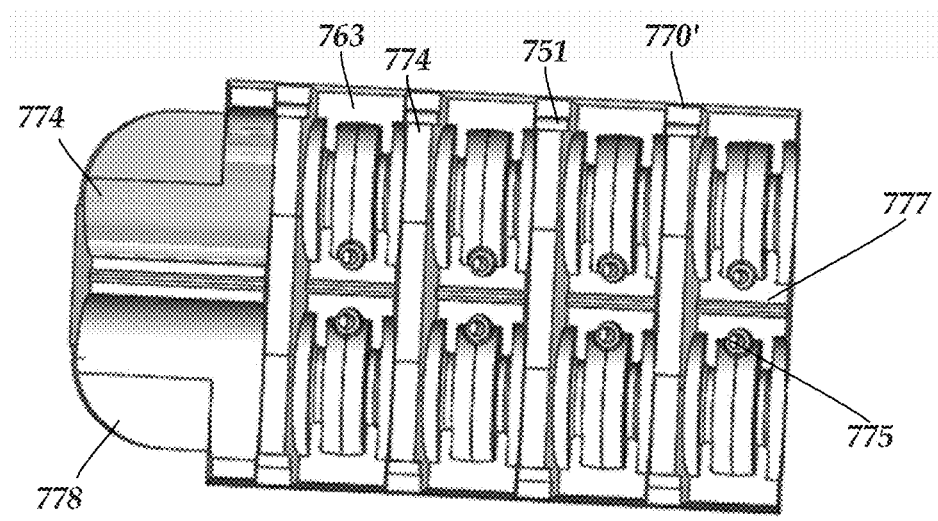
FIG. 9A is a schematic top view one embodiment of a portion of a lower contact housing.
Figure 9B:
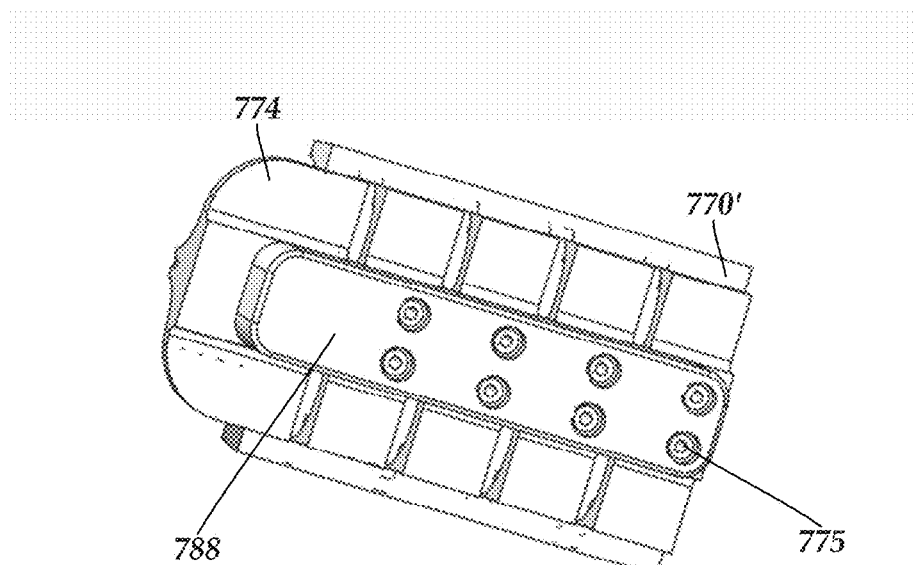
FIG. 9B is a schematic bottom view of one embodiment of a portion of a lower contact housing and ceramic feedthrough.
Figure 9C:
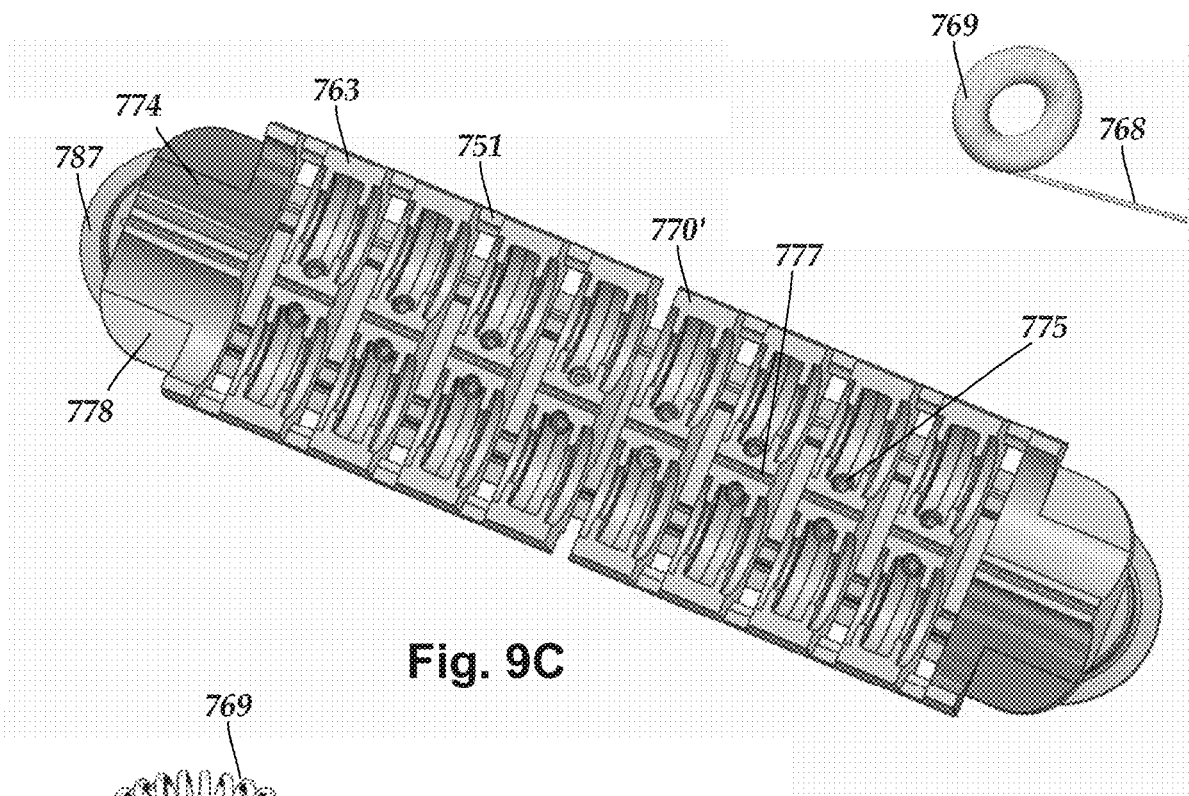
FIG. 9C is a schematic top view one embodiment of a lower contact housing and feedthrough interface, as well as an embodiment of a contact and wire.

FIG. 8A illustrates one embodiment of a lower contact housing 770 which includes multiple receptacles 763. FIGS. 9A to 9C illustrate another embodiment of a lower contact housing 770'. FIG. 9A is a top view and FIG. 9B is a bottom view of a portion of the combined ceramic feedthrough 788 and lower contact housing 770'. FIG. 9C is a top view of the combined ceramic feedthrough 788 and lower contact housing 770' disposed on the ferrule 787.

The lower contact housing 770 may be made of ceramic and can be made of the same ceramic or a different ceramic used in forming the ceramic feedthrough 788. In at least some embodiments, the ceramic feedthrough 788 and lower contact housing 770 are formed together using, for example, molding, such as injection molding.

The lower contact housing 770, 770' includes an optional base 774 (which may be part of the ceramic feedthrough 788) and multiple contact receptacles 763 arranged in one or more rows. The lower contact housing 770' of FIGS. 9A to 9C differs from lower contact housing 770 of FIG. 8A, at least in part, in that the base 774 includes extensions 778 to one or both sides of the rows of contact receptacles 763 and includes outer connections 751 (better viewed in FIG. 7) between the contact receptacles. The extensions 778 may define, in part, one or both of an insertion opening for inserting a lead at one end of each row of contact receptacles 763, a position for a retention block 792 (FIG. 7), or a lead stop at another end of each row of contact receptacles 763.

In the illustrated embodiments, the contact receptacles 763 are arranged in two rows for receiving two proximal lead (or lead extension) ends. In other embodiments, there may be one, three, four, or more rows. In the illustrated embodiments, there are eight contact receptacles in each row for a total of 16 contact receptacles. In other embodiments, there may be any number of contact receptacles per row including, for example, 2, 4, 6, 8, 10, 12, 16 or more contact receptacles in each row.

In at least some embodiments, the lower contact housing 770, 770' includes a channel 777 formed between the contact receptacles 763 for receiving adhesive, as described in more detail below. In at least some embodiments, each of the contact receptacles 763 includes a contact receiving groove 776 formed to receive, and hold in place, one of the contacts 769, as illustrated in FIG. 8A. The contact receiving groove 776 facilitates alignment of the contacts 769 along the connector lumen 767. In at least some embodiments, the contact receptacle 763 in the lower contact housing 770, 770' (and a corresponding receptacle in the upper contact housing 772) can eliminate the use of a separate contact housing (often made of conductive material) disposed around the contact.

Each of the contact receptacles 763 includes a wire hole 775 through the contact receptacle 763, the base 774, and the ceramic feedthrough 788 for receiving a wire 768. FIG. 9C also illustrates one embodiment of a contact 769 with a wire 768 attached to the contact. In at least some embodiments, the wire 768 is inserted into the wire hole 775 and the contact 769 is seated within the contact receiving groove 776 of one of the contact receptacles 763, as illustrated in FIG. 8A. In some embodiments, the wire 768 is attached (for example, by welding) to the contact 769 prior to insertion into the wire hole 775. In other embodiments, the wire 768 is at least partially inserted into the wire hole 775 and then attached (for example, by welding) to the contact 769. As described above, once seated, the wire 768 can be brazed to the ceramic feedthrough (and, optionally, to the contact receptacle 763.) In at least some embodiments, this arrangement of contact 769, wire 768, and wire hole 775 can be easier to manufacture and assemble than corresponding arrangements in conventional connector assemblies.

Figure 10A:
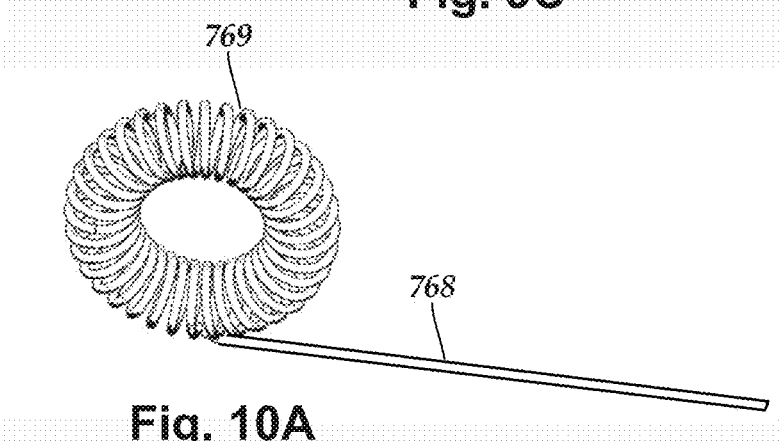
FIG. 10A is a schematic perspective view of one embodiment of a contact and wire.
Figure 10B:
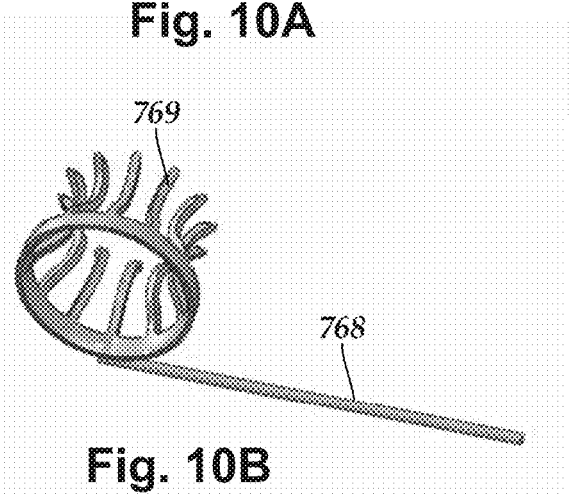
FIG. 10B is a schematic perspective view of another embodiment of a contact and wire.
Figure 10C:
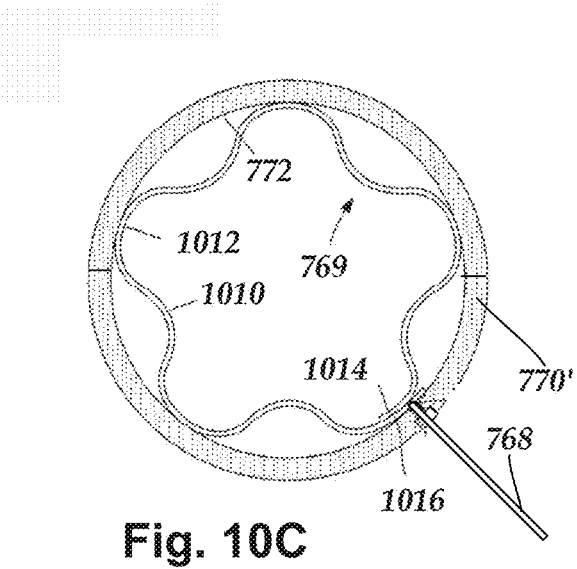
FIG. 10C is a schematic cross-sectional view of a third embodiment of a contact and wire disposed within an upper and lower contact housing.

FIGS. 10A to 10C illustrate different embodiments of suitable contacts 769 with attached wire 768. It will be understood, however, that other contacts can be used. FIG. 10A illustrates one embodiment of a coiled or doughnut-shaped contact 769, such as a canted coil available from Bal Seal Engineering (Foothills Ranch, Calif.). FIG. 10B illustrates one embodiment of a contact 769 that includes bent fingers that receive and contact terminals on a lead or lead extension. Examples of this type of contact and other, similar, suitable contacts can be found in, for example, U.S. Pat. Nos. 9,604,068 and 9,770,598, both of which are incorporated herein by reference in their entireties. FIG. 10C illustrates a shaped wire contact 769 with multiple inward protrusions 1010 for contacting terminals of a lead or lead extension and multiple outward protrusions 1012 for seating within the upper and lower contact housing 772, 770' with overlapping ends 1014, 1016 of wire (for example, platinum/iridium wire). Examples of this type of contact can be found in U.S. Pat. No. 7,803,021, which is incorporated herein by reference in its entirety. Optionally, the ends 1014, 1016 or other parts of the contact 769 can be brazed in place in the upper or lower contact housing 772, 770'. Other examples of suitable contacts can be found in, for example, U.S. Pat. Nos. 7,798,864; 8,046,074; 8,897,876; and 9,656,093; and U.S. Patent Application Publication No. 2018/0028820, all of which are incorporated herein by reference in their entireties. Any other suitable type of contact can be used.

Figure 11A:
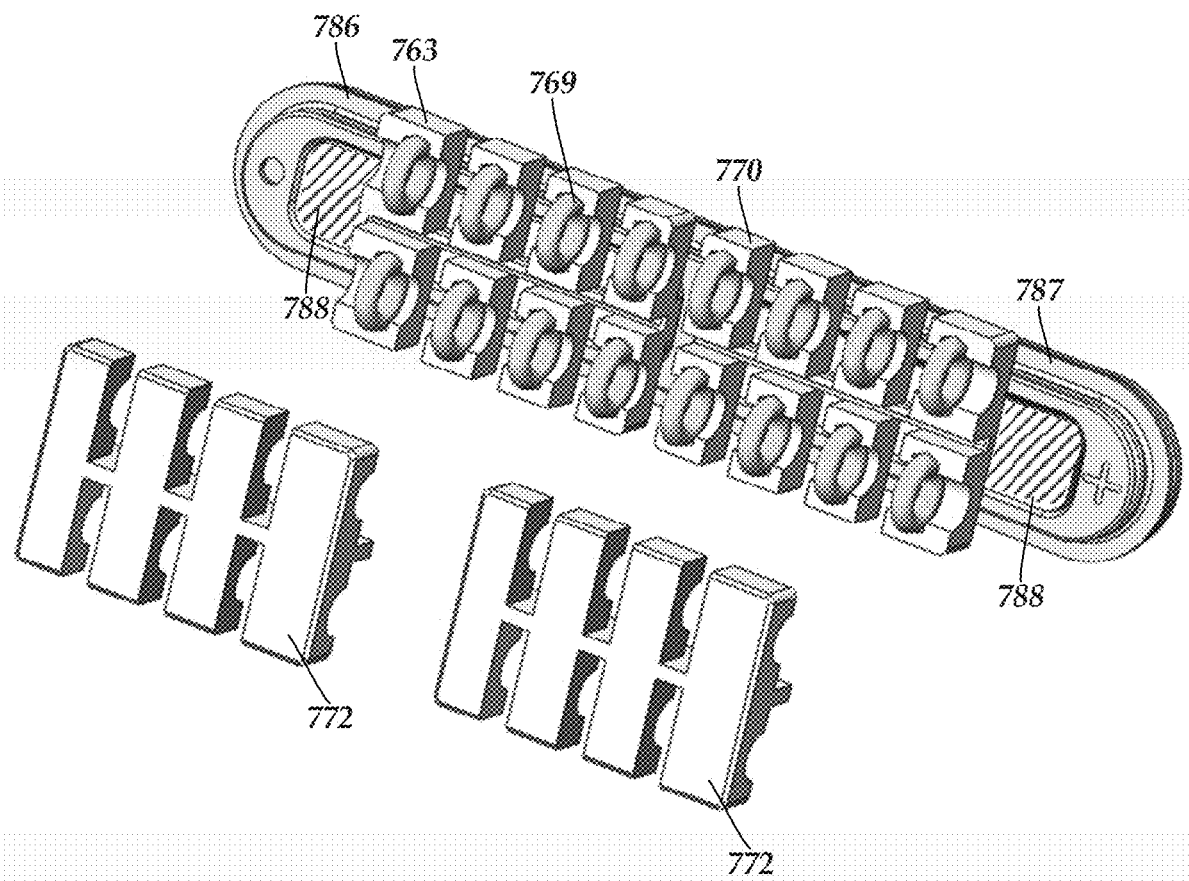
FIG. 11A is a schematic partially exploded view of one embodiment of an upper contact housing, lower contact housing, contacts, and feedthrough interface.
Figure 11B:
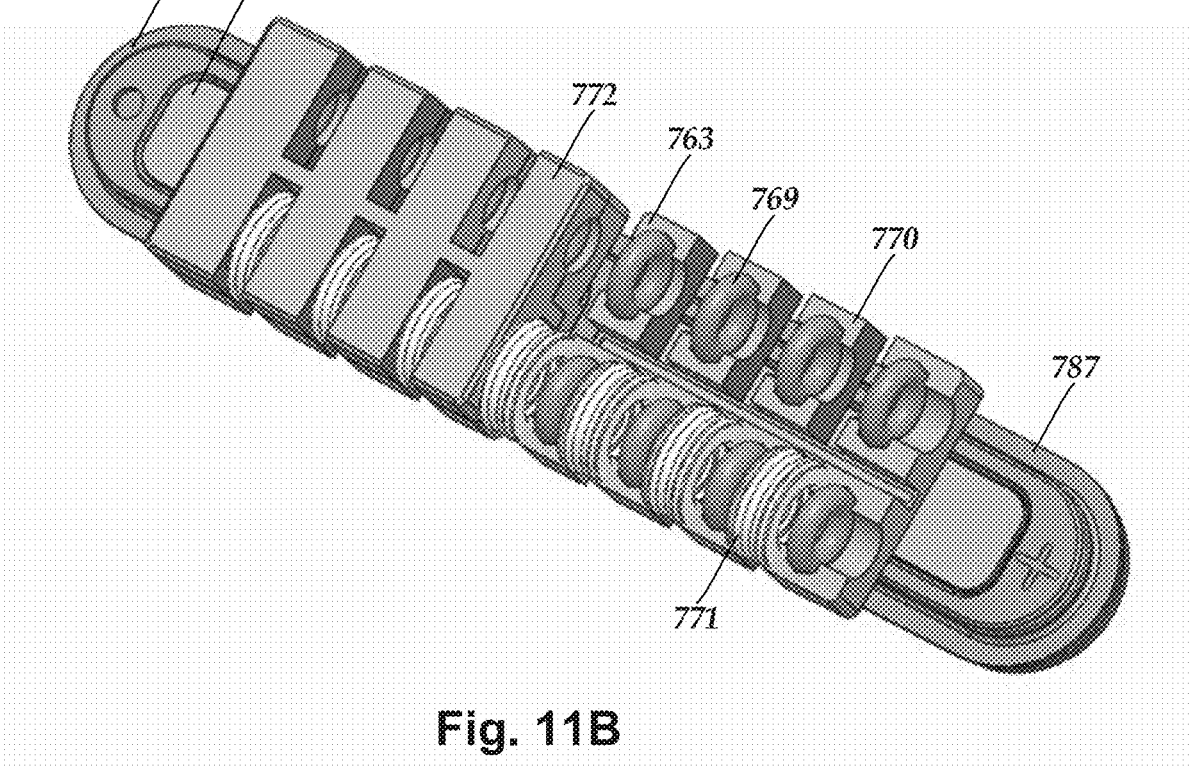
FIG. 11B is a schematic top view of one partially-constructed embodiment of a an upper contact housing, lower contact housing, contacts, spacers, and feedthrough interface.
Figure 11C:
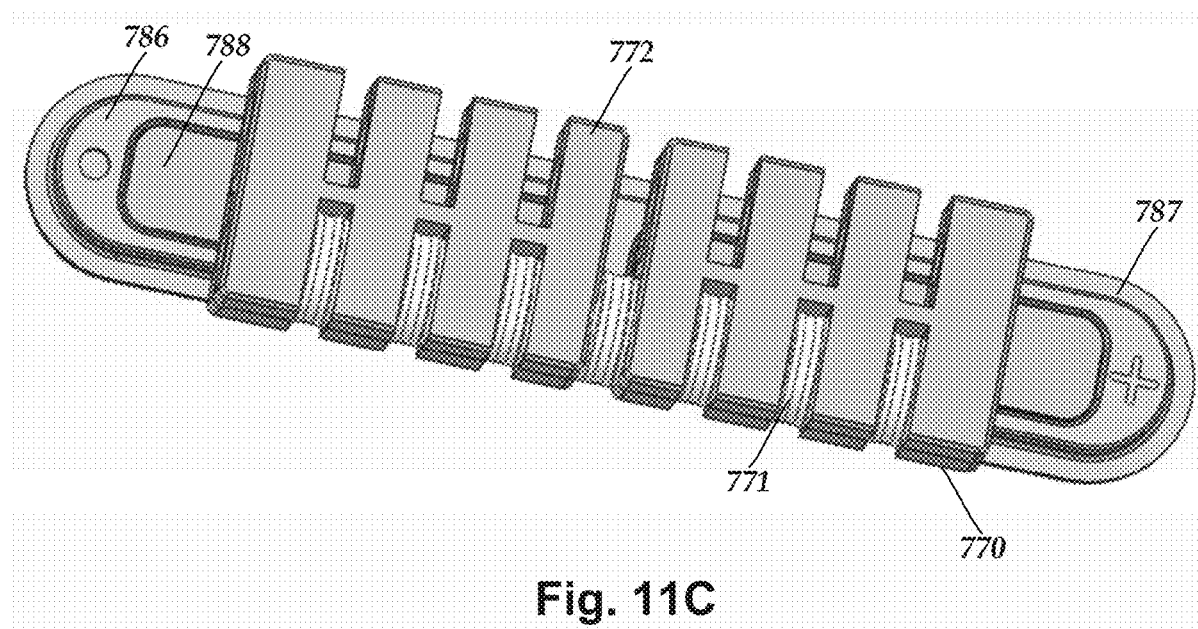
FIG. 11C is a schematic top view of one partially-constructed embodiment of an upper contact housing, lower contact housing, spacers, and feedthrough interface.

In FIG. 11A, the upper contact housing 772 is illustrated prior to attachment to the lower contact housing 770. FIG. 11B illustrates a portion of the upper contact housing 772 attached to the lower contact housing 770 with spacers 771 inserted between the receptacles 763. FIG. 11C illustrates another view of the upper contact housing 772 attached to the lower contact housing 770 with some of the spacers 771 inserted. The lower contact housing 770 can be made of any suitable non-conductive material including, but not limited to, plastic or ceramic materials. The upper contact housing 772 may have receptacles similar to the receptacles 763 in the lower contact housing 770 with a similar contact receiving groove into which the contact 769 fits. The upper and lower contact housings 772, 770 hold the contacts 769 in place within the connector assembly 790. The upper and lower contact housing 772, 770 provide a housing for multiple contacts 769 in contrast the separate contact housings in many conventional connector assemblies.

In at least some embodiments, an adhesive, such as silicone adhesive or epoxy, may be provided in the channel 777 to adhere the lower contact housing 770 to the upper contact housing 772. For example, a syringe may be used to inject the adhesive into the channel 777.

The spacers 771 are made of any suitable non-conductive material including, but not limited to, flexible or resilient plastics, such as silicone, polyurethane, or the like. In at least some embodiments, spacers 771 form a seal between the receptacles in the upper and lower contact housings 772, 770 and may impede or prevent flow of fluid out of the lumen 767 in the connector assembly 790.

In at least some embodiments, an optional retention block 792 (FIG. 7) is attached at the entrance of the connector lumen 767. The retention block 792 may receive a fastener 594 (FIG. 5), such as a screw, pin, or other component, that can interact with the lead or lead extension to hold the lead or lead extension within the connector assembly 790. Examples of retention blocks 792 and fasteners can be found at U.S. Pat. No. 8,548,582; U.S. Patent Application Publication No. 2018/0008832; and U.S. patent application Ser. Nos. 15/878,085 and 15/905,499, all of which are incorporated herein by reference in their entireties.

After the upper and lower contact housings 772, 770 are assembled and the spacers 771 positioned, the connector assembly 790 is essentially complete. Optionally, a connector housing 791 (FIG. 7) can be formed over the remainder of the connector assembly 790. The connector housing 791 can be made of any suitable material including, but not limited to, plastics, such as silicone, polyurethane, epoxy, or the like. The connector housing 791 may be formed by molding, casting, or any other suitable method. In at least some embodiments, the connector housing 791 can be molded over the other components of the connector assembly 790. In other embodiments, the connector housing 791 may be attached over the other components of the connector assembly 790 using an adhesive or mechanical fasteners, such as snaps, screws, bolts, or the like.

Figure 12:
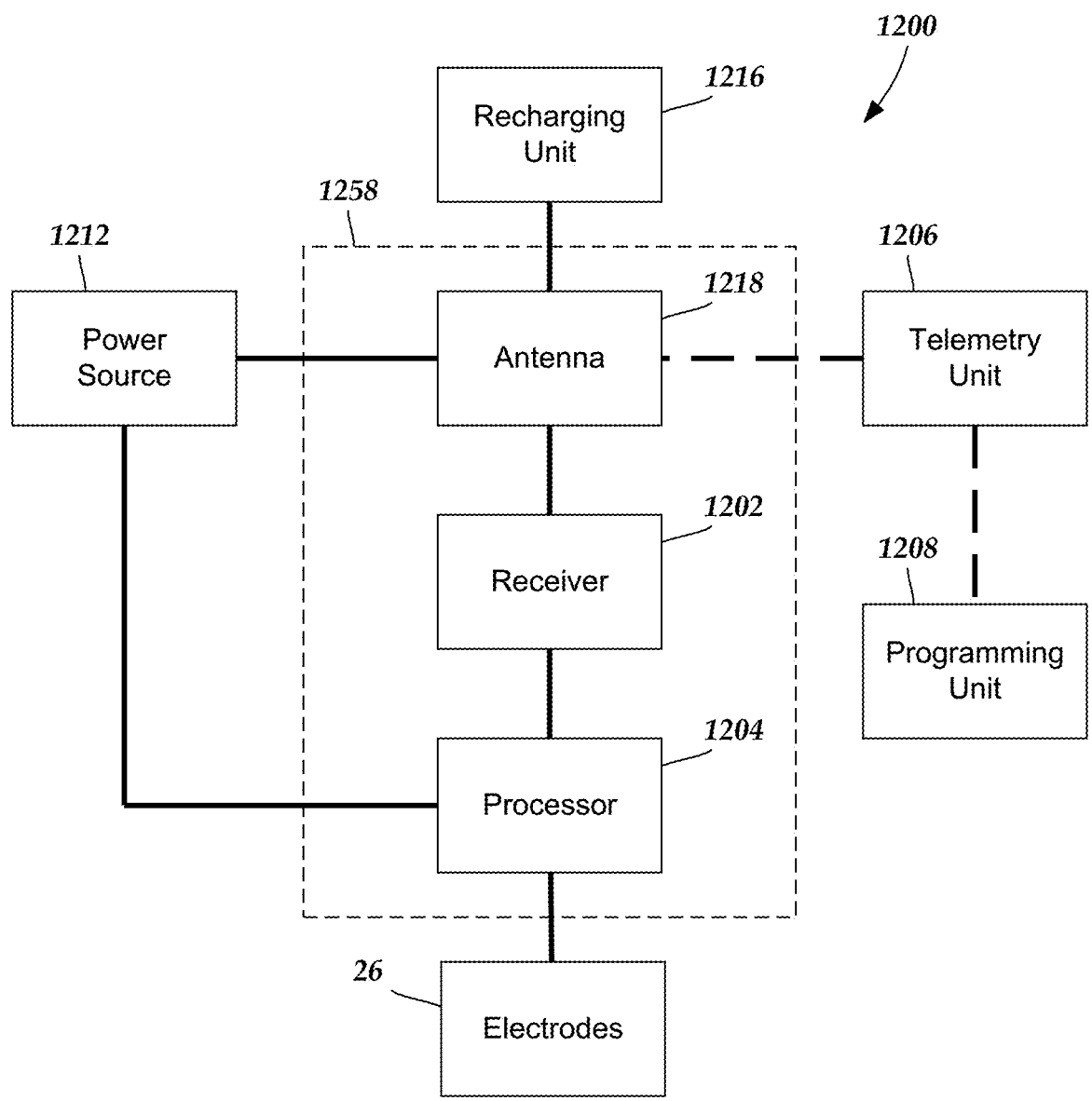
FIG. 12 is a schematic overview of one embodiment of components of a stimulation system, including an electronic subassembly disposed within a control module, according to the invention.

FIG. 12 is a schematic overview of one embodiment of components of an electrical stimulation system 1200 including an electronic subassembly 1258 disposed within a control module. The electronic subassembly 1258 may include one or more components of the IPG. It will be understood that the electrical stimulation system 1200 can include more, fewer, or different components and can have a variety of different configurations including those configurations disclosed in the stimulator references cited herein.

Some of the components (for example, a power source 1212, an antenna 1218, a receiver 1202, and a processor 1204) of the electrical stimulation system 1200 can be positioned on one or more circuit boards or similar carriers within a sealed housing of an implantable pulse generator (see e.g., 14 in FIG. 1), if desired. Any power source 1212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source 1212 through inductive coupling via the optional antenna 1218 or a secondary antenna. In at least some embodiments, the antenna 1218 (or the secondary antenna) is implemented using the auxiliary electrically-conductive conductor. The external power source can be in a device that is mounted on the skin of the user or in a unit that is provided near the user on a permanent or periodic basis.

If the power source 1212 is a rechargeable battery, the battery may be recharged using the optional antenna 1218, if desired. Power can be provided to the battery for recharging by inductively coupling the battery through the antenna to a recharging unit 1216 external to the user. Examples of such arrangements can be found in the references identified above. The electronic subassembly 1258 and, optionally, the power source 1212 can be disposed within a control module (e.g., the IPG 14 or the ETS 20 of FIG. 1).

In one embodiment, electrical stimulation signals are emitted by the electrodes (e.g., 26 in FIG. 1) to stimulate nerve fibers, muscle fibers, or other body tissues near the electrical stimulation system 1200. The processor 1204 is generally included to control the timing and electrical characteristics of the electrical stimulation system 1200. For example, the processor 1204 can, if desired, control one or more of the timing, frequency, strength, duration, and waveform of the pulses. In addition, the processor 1204 can select which electrodes can be used to provide stimulation, if desired. In some embodiments, the processor 1204 selects which electrode(s) are cathodes and which electrode(s) are anodes. In some embodiments, the processor 1204 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1208 that, for example, allows modification of pulse characteristics. In the illustrated embodiment, the processor 1204 is coupled to a receiver 1202 which, in turn, is coupled to the optional antenna 1218. This allows the processor 1204 to receive instructions from an external source to, for example, direct the pulse characteristics and the selection of electrodes, if desired.

In one embodiment, the antenna 1218 is capable of receiving signals (e.g., RF signals) from an external telemetry unit 1206 which is programmed by the programming unit 1208. The programming unit 1208 can be external to, or part of, the telemetry unit 1206. The telemetry unit 1206 can be a device that is worn on the skin of the user or can be carried by the user and can have a form similar to a pager, cellular phone, or remote control, if desired. As another alternative, the telemetry unit 1206 may not be worn or carried by the user but may only be available at a home station or at a clinician's office. The programming unit 1208 can be any unit that can provide information to the telemetry unit 1206 for transmission to the electrical stimulation system 1200. The programming unit 1208 can be part of the telemetry unit 1206 or can provide signals or information to the telemetry unit 1206 via a wireless or wired connection. One example of a suitable programming unit is a computer operated by the user or clinician to send signals to the telemetry unit 1206.

The signals sent to the processor 1204 via the antenna 1218 and the receiver 1302 can be used to modify or otherwise direct the operation of the electrical stimulation system 1200. For example, the signals may be used to modify the pulses of the electrical stimulation system 1200 such as modifying one or more of pulse duration, pulse frequency, pulse waveform, and pulse strength. The signals may also direct the electrical stimulation system 1200 to cease operation, to start operation, to start charging the battery, or to stop charging the battery. In other embodiments, the stimulation system does not include the antenna 1218 or receiver 1202 and the processor 1204 operates as programmed.

Optionally, the electrical stimulation system 1200 may include a transmitter (not shown) coupled to the processor 1204 and the antenna 1218 for transmitting signals back to the telemetry unit 1206 or another unit capable of receiving the signals. For example, the electrical stimulation system 1200 may transmit signals indicating whether the electrical stimulation system 1200 is operating properly or not or indicating when the battery needs to be charged or the level of charge remaining in the battery. The processor 1204 may also be capable of transmitting information about the pulse characteristics so that a user or clinician can determine or verify the characteristics.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A connector assembly for an implantable device, the connector assembly comprising:
    a feedthrough interface comprising a ceramic feedthrough and a ferrule attached to, and forming a perimeter around, the ceramic feedthrough;
    a lower contact housing coupled to the feedthrough interface, wherein the lower contact housing and ceramic feedthrough define a plurality of wire holes extending therethrough;
    an upper contact housing attached to the lower contact housing, the upper and lower contact housings collectively defining a plurality of contact receptacles between the upper contact housing and the lower contact housing and defining at least one lead receiving lumen extending through multiple ones of the contact receptacles and configured to receive a portion of lead or lead extension inserted into the respective lead receiving lumen, each of the contact receptacles defining an opening for at least one of the wire holes, wherein each of the contact receptacles is defined in part by the lower contact housing and in part by the upper contact housing, wherein the lower contact housing is disposed between the ceramic feedthrough and the upper contact housing;
    a plurality of connector contacts, each connector contact disposed in a one of the contact receptacles and defining a lead receiving opening that is aligned with one of the at least one lead receiving lumen; and
    a plurality of wires, each of the wires coupled to one of the connector contacts and extending through one of the wire holes so that the respective wire extends out of the ceramic feedthrough.

2. The connector assembly of claim 1, wherein the lower contact housing is made of ceramic.

3. The connector assembly of claim 2, wherein the lower contact housing and ceramic feedthrough are a single molded ceramic piece.

4. The connector assembly of claim 2, wherein the wires are brazed to the ceramic feedthrough.

5. The connector assembly of claim 4, wherein the wires are brazed to the lower contact housing.

6. The connector assembly of claim 1, wherein the ferrule is attached to the ceramic feedthrough by brazing.

7. The connector assembly of claim 1, wherein the upper contact housing comprises a polymer or ceramic material.

8. The connector assembly of claim 1, further comprising a non-conductive connector housing disposed over the upper and lower contact housings.

9. The connector assembly of claim 1, wherein each of the wires is directly attached to one of the connector contacts.

10. The connector assembly of claim 1, further comprising a plurality of spacers, each spacer disposed between a pair of the contact receptacles.

11. The connector assembly of claim 1, further comprising adhesive coupling the upper contact housing to the lower contact housing.

12. An implantable control module for an electrical stimulation system, the control module comprising:
    the connector assembly of claim 1;
    a housing attached to the feedthrough interface of the connector assembly; and
    an electronic subassembly disposed in the housing and electrically coupled to the wires extending out of the ceramic feedthrough.

13. The implantable control module of claim 12, wherein the ferrule of the connector assembly is welded to the housing.

14. The implantable control module of claim 12, wherein the housing and the feedthrough interface form a hermetically sealed cavity within which the electronic subassembly is disposed.

15. An electrical stimulation system, comprising:
the implantable control module of claim 12; and
an electrical stimulation lead comprising a proximal portion, a distal portion, a plurality of terminals disposed along the proximal portion, a plurality of electrodes disposed along the distal portion, and a plurality of conductors electrically coupling the terminals to the electrodes, wherein the proximal portion of the electrical stimulation lead is configured for insertion into the connector assembly of the implantable control module.

16. The electrical stimulation system of claim 15, further comprising a lead extension comprising a proximal portion, a distal portion, a plurality of terminals disposed along the proximal portion, a connector disposed along the distal portion, a plurality of connector contacts disposed within the connector, and a plurality of conductors electrically coupling the terminals to the connector contacts, wherein the proximal portion of the electrical stimulation lead is configured for insertion into the connector of the lead extension and the proximal portion of the stimulation lead extension is configured for insertion into the connector assembly of the implantable control module.

17. A method of making a connector assembly, the method comprising:
forming a ceramic feedthrough and a lower contact housing with a plurality of contact receptacles in the lower contact housing and a plurality of wire holes with each of the wire holes extending from a contact receptacle through the lower contact housing to an opening on an opposite side of the ceramic feedthrough;
coupling a ferrule to a ceramic feedthrough;
coupling one of a plurality of wires to each of a plurality of contacts;
inserting each of the contacts into a different one of the contact receptacles and, for each of the contacts, inserting the wire coupled to the contact into the wire hole extending from the contact receptacle; and
attaching an upper contact housing to the lower contact housing to hold the contacts within the contact receptacles, wherein each of the contact receptacles is defined in part by the lower contact housing and in part by the upper contact housing, wherein the lower contact housing is disposed between the ceramic feedthrough and the upper contact housing.

18. The method of claim 17, wherein forming the ceramic feedthrough and the lower contact housing comprises molding the ceramic feedthrough and lower contact housing together.

19. The method of claim 17, further comprising inserting spacers between pairs of the contact receptacles.

20. The method of claim 17, wherein coupling the ferrule to the ceramic feedthrough comprises brazing the ferrule and the wires to the ceramic feedthrough.

* * * * *